United States Patent
Nir et al.

(10) Patent No.: US 7,442,781 B2
(45) Date of Patent: Oct. 28, 2008

(54) DIAGNOSIS, PREVENTION AND TREATMENT OF CANCER

(75) Inventors: Uri Nir, Moshav Gimzo (IL); Erez Pery, Ramat Gan (IL); Sally Shpungin, Ramat Gan (IL)

(73) Assignee: Urifer Ltd., Raanana (IL)

( * ) Notice: Subject to any disclaimer, the term of this patent is extended or adjusted under 35 U.S.C. 154(b) by 562 days.

(21) Appl. No.: 10/486,101

(22) PCT Filed: Aug. 15, 2002

(86) PCT No.: PCT/IL02/00675

§ 371 (c)(1), (2), (4) Date: Feb. 9, 2004

(87) PCT Pub. No.: WO03/017817

PCT Pub. Date: Mar. 6, 2003

(65) Prior Publication Data

US 2005/0063973 A1    Mar. 24, 2005

(51) Int. Cl.
- C07H 21/02  (2006.01)
- C07H 21/04  (2006.01)
- A61K 31/70  (2006.01)
- A61K 31/74  (2006.01)

(52) U.S. Cl. ................................. 536/23.1; 536/24.5
(58) Field of Classification Search .................. None
See application file for complete search history.

(56) References Cited

U.S. PATENT DOCUMENTS

| | | |
|---|---|---|
| 3,791,932 A | 2/1974 | Schuurs et al. |
| 3,839,153 A | 10/1974 | Schuurs et al. |
| 3,850,578 A | 11/1974 | Mcconnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,666,828 A | 5/1987 | Gusella |
| 4,683,202 A | 7/1987 | Mullis |
| 4,801,531 A | 1/1989 | Frossard |
| 4,879,219 A | 11/1989 | Wands et al. |
| 5,011,771 A | 4/1991 | Bellet et al. |
| 5,192,659 A | 3/1993 | Simons |
| 5,272,057 A | 12/1993 | Smulson et al. |
| 5,281,521 A | 1/1994 | Trojanowski |
| 6,426,221 B1 | 7/2002 | Ward et al. |

FOREIGN PATENT DOCUMENTS

WO    WO 01/90337    * 11/2001

WO    WO 02/40717    * 5/2002

OTHER PUBLICATIONS

Hohjoh et al, FEBS Letters, Jun. 2002, vol. 521, pp. 195-199.*
Kurreck (Journal of Biomedicine and Biotechnology, 2006, pp. 1-7).*
Tolcher et al (Clinical Cancer Research, 2002, vol 8, pp. 2530-2535).*
Cripps et al (Clinical Cancer Research. 2002, 8, pp. 2188-2192).*
Marshall et al (Clinical Colorectal Cancer, 2004, vol. 4, pp. 268-274).*
Oza et al (Gynecological Oncology, 2003, vol. 89, pp. 129-133).*
Verma et al (Nature, 1997, vol. 389, pp. 239-242).*
Eck et al (Gene-Based Therapy, In: The Pharmacological Basis of Therapeutics, Goodman and Gilman, Ed.s, 1996, pp. 77-101.*
Schultze et al (Trends in Immunology, 2004, vol. 25, pp. 659-664).*
Bodey et al, (Anticancer Research, 2000, vol. 20, pp. 2665-2676).*
Abstract of Vile et al (Gene Therapy, 2000, vol. 7, pp. 2-8).*
Addissson et al (PNAS, vol. 92, pp. 8522-8526.*
Garcia, J.A. et al. (1992) Proc.Natl.Acad.Sci.USA 89:9372-9376 "Cloning and chromosomal mapping of a human immunodeficent virus 1 "TATA" element modulatory factor".
OMIM 601126, Locus ID 7110, GenBank L01042.
Hsiao, et al; (1999) J. Biol. Chem. 274, 22373-22379; "Isolation and Characterization of ARA160 as The First Androgen Receptor N-Terminal—Associated Coactivator In Human Prostate Cells".
Schwartz, et al., (1998) FEBS Lett. 434, 339-345) "Tyrosine phosphorylation of the TATA element modulatory factor by the FER nuclear tyrosine kinases".
Pawson, et al. (1989) Mol. Cell. Biol. 9, 5722-5725; "The FER Gene Is Evolutionarily Conserved And Encodes a Widely Expressed Member Of The EPS/FES Protein-Tyrosine Kinase Family".
Paulson, et al. (1997) Oncogene 14, 641-652 "The Dfer gene of Drosophila melanogaster encodes two membrane-associated proteins that can both transform vertebrate cells".
Letwin, et al. (1988) Oncogene 3, 621-627 "Novel protein-tyrosine kinase cDNAs related to fps/fes and eph cloned using anti-phosphotyrosine antibody".
Hao et al; 1989 Mol. Cell. Biol. 9, 1587-1593 Isolation and Sequence Analysis of a Novel Human Tyrosine Kinase Gene.
Hao, et al (1991) Mol. Cell. Biol. 11, 1180-1183 Nuclear and Cytoplasmic Location of the FER Tyrosine Kinase.
Kim, et al. (1998) J. Biol. Chem. 273, 23542-23548 "Growth Factor-dependent Phosphorylation of the Actin-binding Protein Cortactin is mediated by the Cytoplasmic Tyrosine Kinase FER".

(Continued)

Primary Examiner—Karen A Canella
(74) Attorney, Agent, or Firm—The Nath Law Group; Susanne M. Hopkins; Ari G. Zytcer

(57) ABSTRACT

Methods and compositions for the diagnosis, prevention, and treatment of cancer are provided. More particularly, the present invention provides methods and compositions for the diagnosis, prevention, and treatment of cancer through detection and modulation of the expression of TMF/ARA160 and Fer.

6 Claims, 19 Drawing Sheets

OTHER PUBLICATIONS

Halachmy, et al. (1997) Oncogene 14, 2871-2880 p94fer facilitates cellular recovery of gamma irradiated pre-T cells.
Rosato, et al (1998) Mol. Cell. Biol. 18, 5762-5770 "Involvement of the Tyrosine Kinase Fer in Cell Adhesion".
Priel-Halachmi, et al (2000) J. Biol. Chem. 275, 28902-28910 "FER Kinase Activation of Stat3 is determined by the N-terminal sequence".
Kim,L and Wong,T.W (1995) Molecular & Cellular Biology "The Cytoplasmic Tyrosine Kinase FER is associated with the Catenin-Like Substrate pp120 and is actived by growth factors".
Craig, et al. (2001) Mol. Cell Biol. 21, 603-613 "Mice Devoid of Fer Protein-Tyrosine Kinase Activity Are Viable and Fertile but Display Reduced Cortactin Phosphorylation".
Allard, et al (2000) Mol. Cell Endocrinol. 159, 63-77 "Links between Fe tyrosine Kinase expression levels and prostate cell proliferation".
Orlovsky, et al. (2000) Biochemistry 39, 11084-11091 "N-Terminal sequences direct the autophosphorylation states of the FER Tyrosine Kinases in Vivo".
Fischman, et al. (1990) Mol. Cell. Biol. 10, 146-153 "A Murine fer Testis-Specific Transcript (ferT) encodes a truncated Fer Protein".
Hazan, et al. (1993) Cell Growth Differ. 4, 443-449 "ferT encodes a Meiosis—specific Nuclear Tyrosine Kinase".
Marx, J. Science (2001) 292: 2231-2233 "Why some Leukemia Cells Resist STI-571".
Ben-Dor et al. Cell Growth Differ 1999;10:113-29 "Cell cycle-dependent Nuclear accumulation of the p94fer Trosine Kinase is regulated by its NH2 Terminus and is affected by Kinase Domain Integrity and ATP Binding".
Craig et al. Biol Chem 1999;274:19934-42 "Disruption of coiled-coil domains in Fer Protein-tyrosine Kinase Abolishes Trimrization but not Kinase Activation".
Arregui et al Cell Biol 2000;149-1263-74 "The Nonreceptor Tyrosine Kinase Fer mediates Cross-talk between N-Cadherin and β1-Integrins".
Sharp, P. A. Genes Dev 15: 485-490, 2001 RNA interference—2001.
Hannon, G.J. Nature 418: 244-251, 2002 RNA interference.
Fire, A. et al. Nature 391: 806-811, 1998 "Potent and specific genetic interference by double stranded RNA in caenorhabditis elegans".
Caplen, et al. Proc Natl Acad Sci USA 98, 9742-9747, 2001 "Specific inhibition of gene expression by small double-stranded RNA's in invertebrate and vertebrate systems".
Elbashir, et al Genes Dev 15:188-200, 2001 "RNA interference is mediated by 21 and 22 nucleotide RNAs".
Elbashir, et al. Nature 411:494-498, 2001 "Duplexes of 21-nucleotide RNA's mediate RNA interference in cultured mammalian cells".
Brummelkamp, et al. Science 296:550-553, 2002 "A system for stable Expression of short interfering RNAs in Mammalian cells".
Tuschl, T. Nature Biotechnology 20:446-448, 2002 "Expanding small RNA interference".
Paul, et al.. Nature Biotechnology 20:505-508, 2002 "Effective expression of small interfering RNA in human cells".
Lee, N.S., Dohjima, T., Bauer, G., et al. Nature Biotechnology 20:500-505, 2002 "Expression of small interfering RNAs targeted against HIV-1 rev transcripts in human cells".
Tuschl, et al Genes Dev 13: 3191-3197 (1999) "Targeted mRNA degradation by double stranded RNA in vitro".
The siRNA user guide [http://www.mpibpc.gwdg.de/abteilungen/100/105/sirna.html].
Elbashir SM, Harborth J, Weber K, Tuschl T. Methods Feb;26(2):199-213, (2002).
Nat Genet publication ahead of print; doi:10.1038/ng944, 2002 "Efficient delivery of siRNA for inhibition of gene expression in postnatal mice".
Tartakoff, et al. (1983) J. Cell Biol. 97, 1243-1248 "Lectin-Binding Sites As Markers Of Golgi Subcompartments: Proximal-To-Distal Maturation Of Oligosaccharides".
Bloom, et al (1989) J. Biol. Chem. 264, 16083-16092 "A novel 58-kDa Protein Associates with the Golgi Apparatus and Microtubes".
Reaves, et al. (1992) J. Cell Biol. 116, 85-94 Perturbation of the Morphology of the trans-Golgi Network following Brefeldin A treatment : Redistribution of a TGN-specific Integral Membrane Protein TGN38.
Robineau, et al., (2000) Proc. Natl. Acad. Sci. U. S. A. 97, 9913-9918 "Binding site of brefeldin A at the interface between the small G protein ADP-ribosylation factor 1 (ARF1) and the nucleotide-exchange factor Sec7 domain".
Lippincott-Schwartz, et al. (1991) Cell 67, 601-616 "Brefeldin A's Effectson Endosomes, Lysosomes and the TGN Suggest a General Mechanism for regulating Organelle Structure and Membrane Traffic".
Bromberg, et al (1999) Cell 98, 295-303 "Stat3 as an Oncogene".
Zhou, et al (2001) Oncology 60, 330-338 "Interferon Alpha Induction of Stat1 and Stat2 and their prognostic significance in Carcinoid Tumors".
Sinibaldi, et al (2000) Oncogene 19, 5419-5427 Induction of p21 WAF1/CIP1 and cyclin D1 expression by the Src oncoprotein in mouse fibroblasts: role of activated STAT3 signaling.
Bienvenu, et al. (2001) J. Biol. Chem. 276, 16840-16847 Cyclin d1 Represses Stat3 Activation through a Cdk4-independent Mechanism.
Daino, et al (2000) Blood 95, 2577-2585 "Induction of apoptosis by extracellular ubiquitin in human hematopoietic cells; possible involvement of STAT3 degradation by proteasome pathway in interleukin 6-dependent hematopoietic cells".
DeSalle, et al (2001) FEBS Lett. 490, 179-189 "Regulation of the G1 to S transition by the ubiquitin pathway".
Conaway, et al. (1998) Biochim. Biophys. Acta 1377, M49-M54 "The Elongin BC complex and the von Hippel-Lindau tumor suppressor protein".
Kamura, et al. (2001) J. Biol. Chem "Degradation of p27KIPI and the G0-G1 Transition Mediated by a Skp2- independent Ubiquitination Pathway".
Salzberg, et al. (2000) Exp. Cell Res. 254, 45-54 "Expression of a PKR Dominant- Negative Mutant in Myogenic cells Interferes with the Myogenic Process".
Conejo, et al (2001) J. Cell Physiol 186, 82-94 "Insulin Produces Myogenesis in C2C12 Myoblasts by Induction of NF-κB and Downregulation of AP-1 Activites".
Scheffler, I. E. (2001) Adv. Drug Deliv. Rev. 49, 3-26 "Mitochondria make a come back".
Chapman, et al; (1999) Mol. Urol. 3, 11-16 Mechanism of Brefeldin A-Induced Growth Inhibition And Cell Death In Human Prostatic Carcinoma Cells.
Keshet, E. et al., "The Testis-Specific Transcript (ferT) of the Tyrosine Kinase FER Is Expressed during Spermatogenesis in a Stage-Specific Manner", *Molecular and Cellular Biology*, vol. 10, No. 9, pp. 5021-5025 (Sep. 1990).
Campbell et al., "General Properties and Applications of Monoclonal Antibodies", *Laboratory Techniques in Biochemistry and Molecular Biology*, vo. 13, Chap. 1, pp. 1-32 (1984).

* cited by examiner

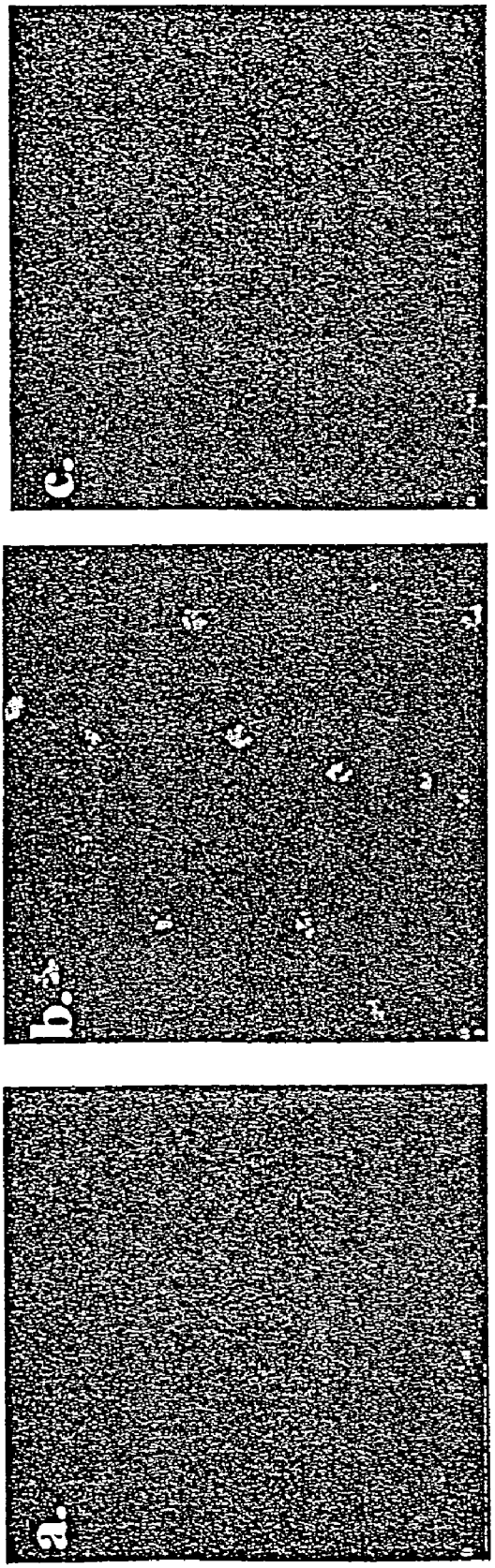

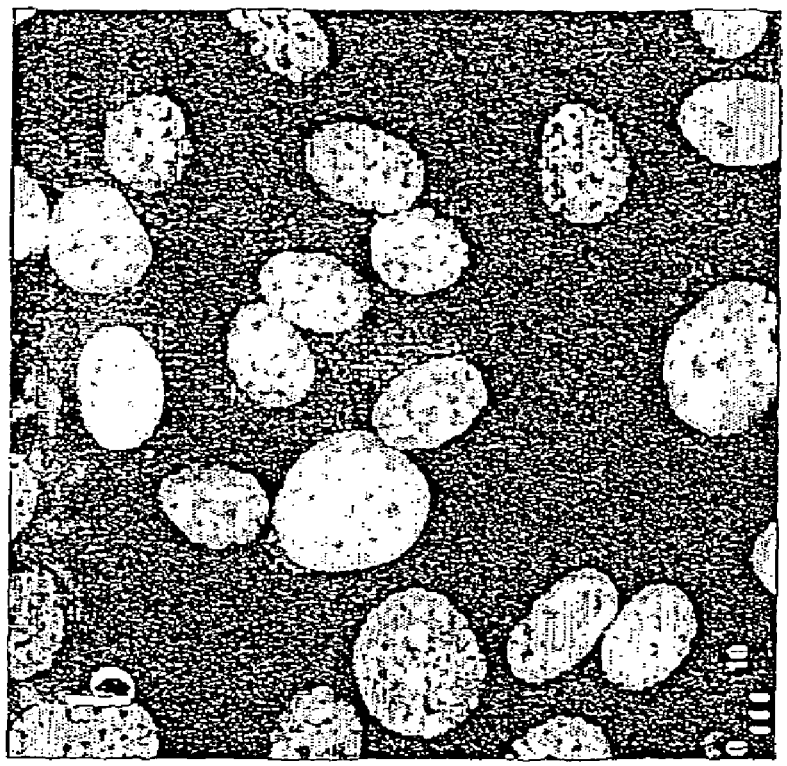
Fig. 2B-b
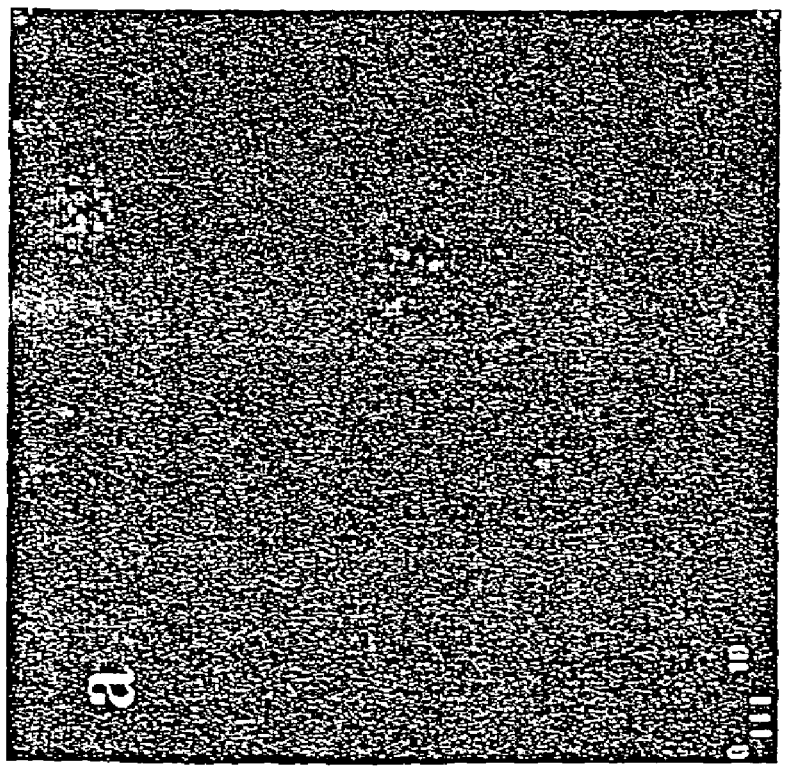
Fig. 2B-a

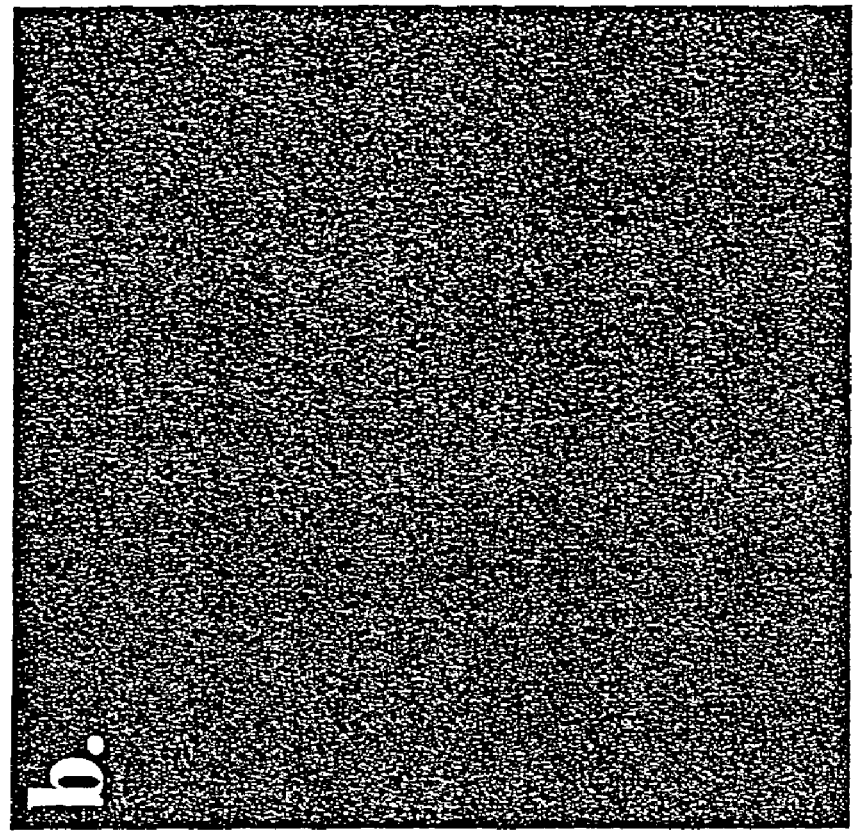
Fig. 3A-b
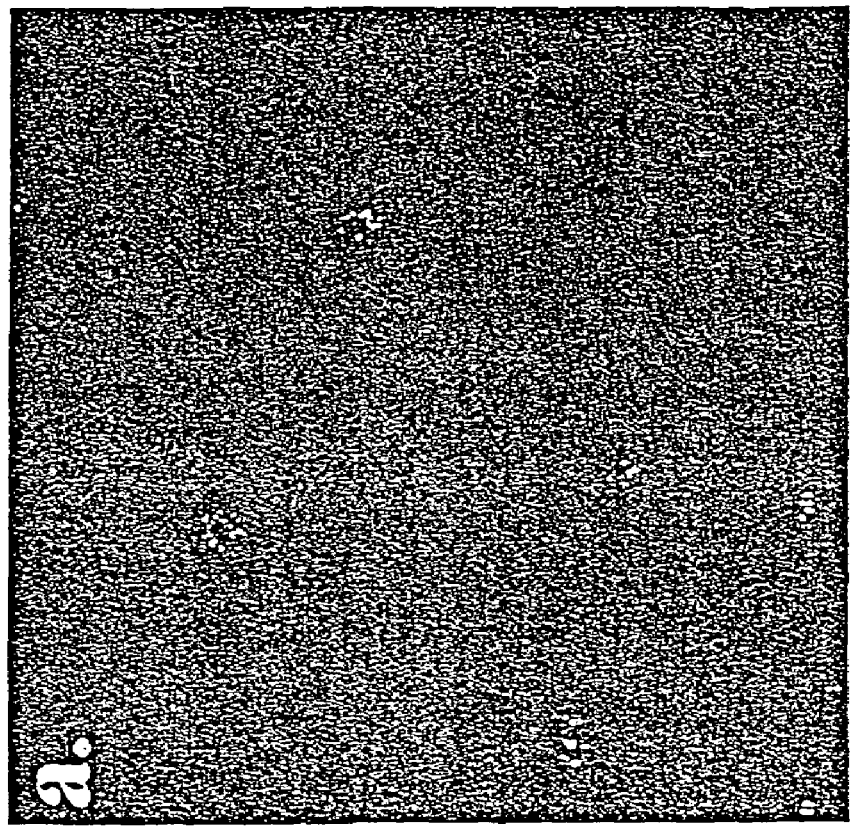
Fig. 3A-a

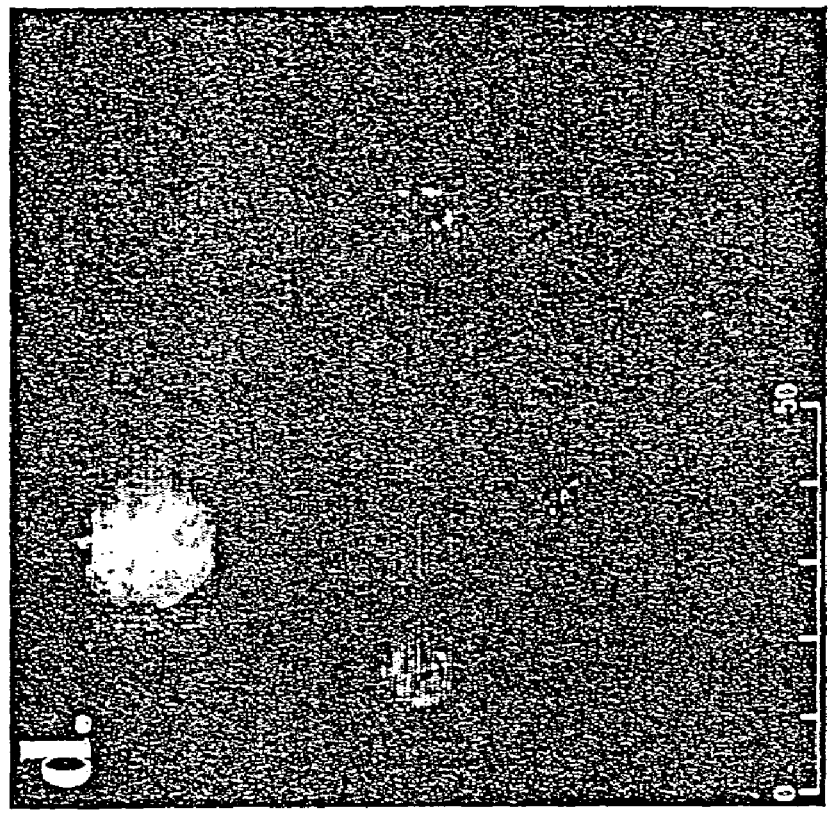
Fig. 3A-d
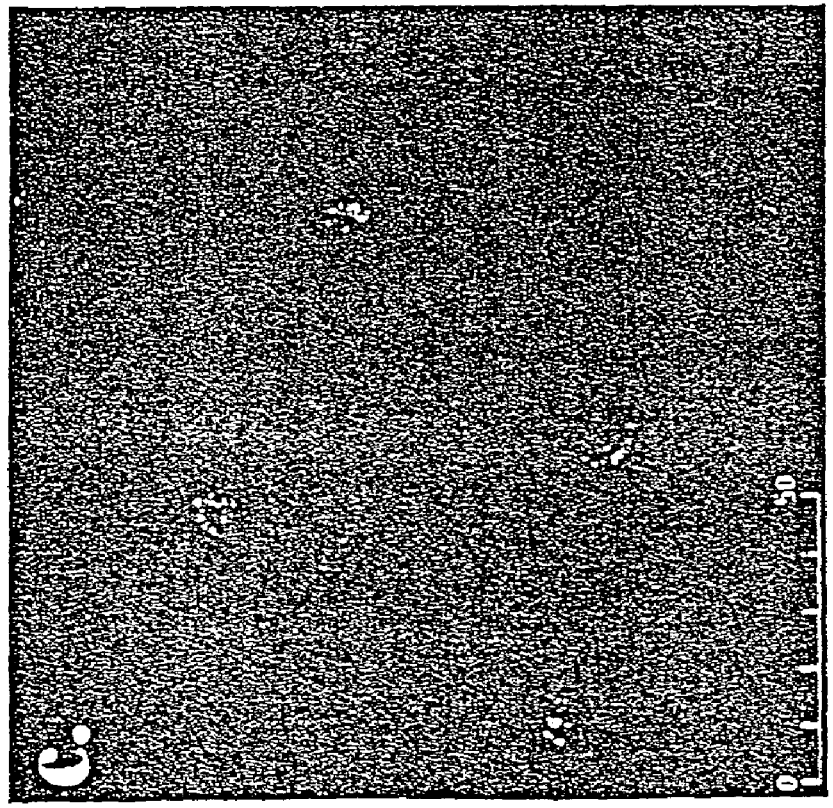
Fig. 3A-c

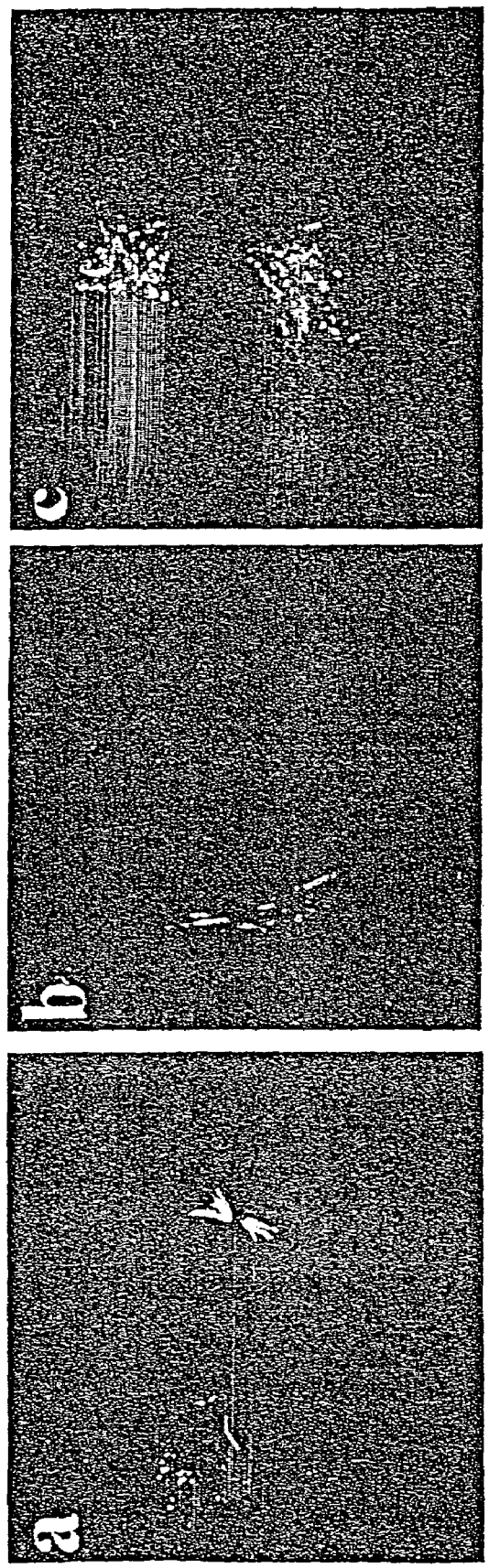

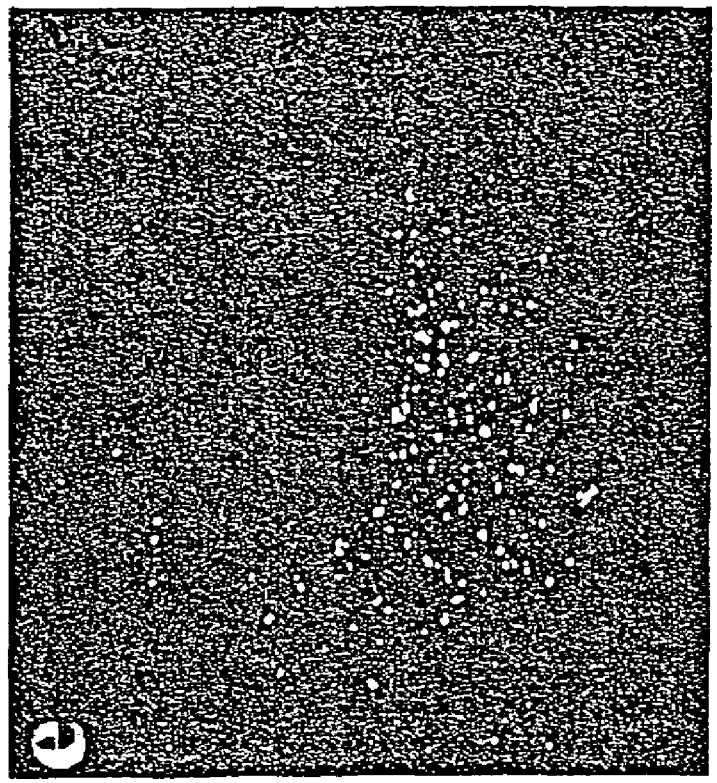
Fig. 3B-e
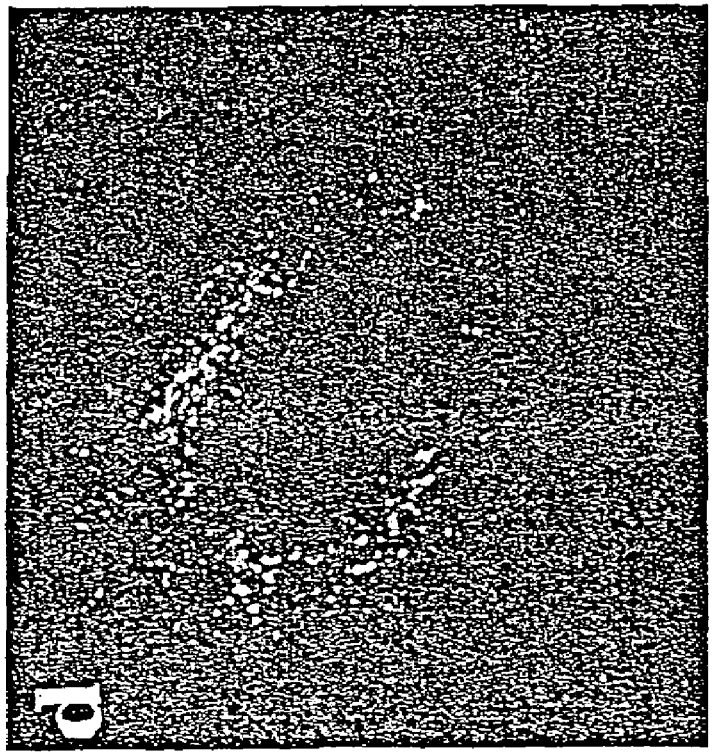
Fig. 3B-d

Treatment of -PC3 - prostate cancer cells with siRNA directed toward the Fer mRNA (protein levels).

Interference

Control

Control

DIAGNOSIS, PREVENTION AND TREATMENT OF CANCER

FIELD AND BACKGROUND OF THE INVENTION

The present invention relates to methods and compositions for the diagnosis, prevention, and treatment of cancer in mammals, and in particular, humans. More particularly, the present invention relates to methods and compositions for the diagnosis, prevention, and treatment of cancer through detection and modulation of the expression of TMF/ARA160 and Fer.

Cancer is one of the top killing diseases in the western world and vast amounts of effort and financial resources are being invested in developing novel therapeutic approaches. However, the need for reliable diagnostic tools, is a rate-limiting step in the successful application of a cancer therapy. This is best manifested by the fact that most of the currently known markers of cancers, are reliable at the level of only 30-50%. Thus the need for new markers that could be reliably used in the detection of a wide variety of cancers, exists Further, there is a generally accepted need for improved methods of cancer prevention and treatment, devoid of the well known side effects of current therapies. There is thus a widely recognized need for, and it would be highly advantageous to have, methods and compositions for the diagnosis of cancer that can distinguish the development of the malignant state and for methods and compositions for prevention and treatment of cancer.

A protein termed TMF or ARA60, which is present in a dormant form in normal mammalian cells has been recently identified (Garcia, J. A. et al. (1992) Proc. Natl. Acad. Sci. USA 89:9372-9376) [OMIM 601126, Locus ID 7110, GenBank L01042] Several functions have been attributed to TMF. It was initially identified as a DNA binding protein that preferentially binds to the TATA element in the human immunodeficiency 1 (HIV1) long terminal repeat (LTR) Thus, TMF/ARA160 was initially identified as a transcription factor that can suppress transcription of RNA Polymerase II genes by binding to their TATA box thus giving it the name TATA Element Regulatory Factor (TMF) (Garcia, J. A. et al. (1992) Proc. Natl. Acad. Sci. USA 89:9372-9376). Later, TMF was shown to function as a co-activator of nuclear receptors, particularly the androgen receptor (AR) (Hsiao, P. W. et al. (1999) J. Biol. Chem. 274:22373-22379), a fact that gained it the name androgen receptor coactivator 160 kDa, or ARA160 (Hsiao, P.-W. et al. (1999) J. Biol. Chem. 274:22373-22379).

TMF consists of 1093 amino acids with an apparent molecular mass of 160 kDa (Hsiao, P. W. at Chang, C. (1999) J. Biol. Chem. 274, 92373-29379; Garcia, J. A., Ou, S. H., Wu, F., Lusis, A. J., Sparkes, R. S. & Gaynor, R. B. (1992) Proc. Natl. Acad. Sci. USA 89, 9372-9376). The central and c-terminal parts of TMF/ARA160 contain coiled coil forming domains (cc) that could mediate the interaction of that protein with other cellular factors. Using a yeast two hybrid screening system (Schwartz, Y., Ben-Dor, I., Navon, A., Motro, B. & Nir, U. (1998) FEBS Lett 434, 339-345) it has been found that TMF/ARA160 interacts Edith Fer tyrosine kinases and modulates their activities. The Fer and AR binding domains in TMF/ARA160, overlap and both include cc forming sequences.

Fer (p94$^{fer}$) is an evolutionarily conserved (Pawson, T., Letwin, K., Lee, T., Hao, Q.-L., Heisterkamp, N. & Groffen, J. (1989) Mol. Cell. Biol. 9, 5722-5725; Paulson, R., Jackson, J., Immergluck, K. & Bishop, J. M. (1997) Oncogene 14, 641-652) and ubiquitously expressed tyrosine kinase that resides mainly in the cytoplasm and nucleus of expressing cells (Letwin, K., Yee, S.-P. & Pawson, T. (1988) Oncogene 3, 621-627; Hao, Q.-L., Heisterkamp, N. & Groffen, J. (1989) Mol. Cell. Biol. 9, 1587-1593; Hao, Q.-L., Ferris, D. K., White, G., Heisterkamp, N. & Groffen, J. (1991) Mol. Cell. Biol. 11, 1180-1183; Kim, L. & Wong, T. W. (1998) J. Biol. Chem. 273, 23542-23548) [OMIM 176942, Locus ID 2241, GenBank J03358]. Fer vas not detected in mourn pert and T cell lines (Halachmy, S., Bern, O., Schreiber, L., Carmel, M., Sharabi, Y., Shoham, J. & Nir, U. (1997) Oncogene 14, 2871-2880).

In the cytoplasm, Fer associates with cell adhesion molecules (Kim, L. & Wong, T. W. (1998) J. Biol. Chem. 273, 23542-23548; Rosato, R., Veltmaat, J. M., Groffen, J. & Heisterkamp, N. (1998) Mol. Cell. Biol. 18, 5762-5770) and Stat3 (Priel-Halachmi, S., Ben-Dor, I., Shpungin, S., Tennenbaum, T., Molavani, H., Bachrach, M., Salzberg, S. & Nir, U. (2000) J. Biol Chem. 275, 28902-28910) and its kinase activity increases in growth factor stimulated cells (Kim, L and Wong, T. W (1995) Molecular & Cellular Biology). However, no direct role has been attributed to Fer in the establishment of adherens junctions or focal adhesions (Craig, A. W., Zimgibl, R., Williams, K. Cole, L. A & Greer, P. A. (2001) Mol. Cell Biol. 21, 603-613), nor was Fer found to be essential for growth factor dependent activation of Stat3. The function of Fer is redundant in the mouse, and mice devoid of a functional Fer are viable and fertile (Craig, A. W., Zimgibl, R., Williams, K., Cole, L A. & Greer, P. A. (2001) Mol. Cell Biol. 21, 603-613). However, the functioning of Fer was found to be pivotal for the proliferation of malignant cell lines (Allard, P., Zoubeidi, A, Nguyen, L. T., Tessier, S., Tanguay, S., Chevrette, M., Aprikian, A. & Chevalier, S. (2000) Mol. Cell Endocrinol. 159, 63-77; Orlovsky, K., Ben-Dor, I, Priel-Halachmi, S., Malovany, H. & Nir, U. (2000) Biochemistry 39, 11084-11091) Thus, Fer could be linked to the proliferation of mammalian cells.

A testis specific variant of Fer, termed p51$^{ferT}$, is encoded by an alternatively spliced FER transcript (Fischman, K, Edman, J. C., Shackleford, G. M., Turner, J. A., Rutter, W. J. & Nir, U. (1990) Mol. Cell Biol 10, 146-153; Keshet, E., Itin, A, Fischman, K. & Nir, U. (1990) Mol. Cell. Biol. 10, 5021-5025). Fer and p51$^{ferT}$ share identical SH2 and kinase domains but they differ in their N-teminal tails (Hao, Q.-L., Heisterkamp, N. & Groffen, J. (1989) Mol. Cell. Biol. 9, 1587-1593; Fischman, K., Edman, J. C., Shackleford, G. M, Turner, J. A., Rutter, W. J. & Nir, U. (1990) Mol. Cell. Biol. 10, 146-153). p51$^{ferT}$ accumulates in late primary spermatocytes (Hazan, B., Bern, O., Carmel, M., Lejbkowicz, F., Goldstein, R. S. & Nir, U. (1993) Cell Growth Differ. 4, 443-449). However the role of that kinase in the spermatogenic process is also not understood (Craig, A. W., Zirngibl, R., Williams, K., Cole, L. A. & Greer, P. A. (2001) Mol. Cell Biol. 21, 603-613).

The activities attributed so far to TMF/ARA160 have not been linked to the Fer tyrosine kinase. Further, it has not heretofore been demonstrated that levels of expression of TMF/ARA160 can be measured or altered for diagnosis, prevention, or treatment of cancer. Specific modulation of expression of TMF/ARA160 and of Fer for prevention and treatment of cancer have not been developed Consequently there is an unmet need for agents and methods capable of effectively detecting the expression of TMF/ARA160 for the diagnosis of cancer and for modulation of expression of Fer and of TMF/ARA160 for prevention and treatment of cancer.

SUMMARY OF THE INVENTION

The present invention is directed to methods and compositions for the diagnosis, prevention, and treatment of cancer. More particularly, the present invention provides methods and compositions for the diagnosis, prevention, and treatment of cancer through detection and modulation of the expression of TMF/ARA160 and Fer.

According to one aspect of the present invention there is provided an antibody that binds specifically to TMF/ARA160 protein.

According to another aspect of the present invention there is provided a kit for detection of TMF/ARA160 protein in a sample, the kit including the antibody that binds specifically to TMF/ARA160 protein.

According to yet another aspect of the present invention there is provided a method of detecting TMF/ARA160 in a biological sample which includes providing the biological sample, contacting the biological sample with the antibody that binds specifically to TMF/ARA160 protein, and detection binding of the antibody to the TMF/ARA160 protein in the sample.

According to still another aspect of the present invention there is provided a method of diagnosing a malignant tumor in an individual, which includes providing a biological sample, contacting the biological sample with the antibody that binds specifically to TMF/ARA160 protein, and detecting binding of the antibody to a TMF/ARA160 protein in the sample.

According to further features in preferred embodiments of the invention described below, the method of diagnosing a malignant tumor in an individual further includes diagnosing the malignant tumor if the binding of the antibody is absent in the sample.

According to an additional aspect of the present invention there is provided a method of treating cancer in an individual, which includes increasing a level of TMF/ARA160 protein in cells or tissues of the individual.

According to yet an additional aspect of the present invention there is provided a compound 21 nucleobases in length having the nucleotide sequence corresponding to SEQ ID NO:2 below. According to yet an additional aspect of the present invention there is provided a compound 21 nucleobases in length having the nucleotide sequence corresponding to SEQ ID NO:3 below. According to yet an additional aspect of the present invention there is provided a compound 21 nucleobases in length having the nucleotide sequence corresponding to SEQ ID NO:5 below. According to yet an additional aspect of the present invention there is provided a compound 21 nucleobases in length having the nucleotide sequence corresponding to SEQ ID NO:6 below.

According to yet an additional aspect of the present invention there is provided a short interfering ribonucleic acid molecule, which is a duplex molecule of two compounds, wherein the first compound is the compound of 21 nucleobases in length having the nucleotide sequence corresponding to SEQ ID NO:2 below, and the second compound is the compound of 21 nucleobases in length having the nucleotide sequence corresponding to SEQ ID NO:3 below. According to yet an additional aspect of the present invention there is provided a short interfering ribonucleic acid molecule, which is a duplex molecule of two compounds, wherein the first compound is the compound of 21 nucleobases in length having the nucleotide sequence corresponding to SEQ ID NO:5 below, and the second compound is the compound of 21 nucleobases in length having the nucleotide sequence corresponding to SEQ ID NO:6 below.

According to yet an additional aspect of the present invention there is provided a kit for the treatment of cancer including at least one short interfering ribonucleic acid molecule, where the short interfering ribonucleic acid molecule is directed against fer mRNA, the short interfering ribonucleic acid molecule selected from the siRNAs described above.

According to yet an additional aspect of the present invention there is provided a pharmaceutical preparation comprising at least one short interfering ribonucleic acid molecule, where the short interfering ribonucleic acid molecule is directed against fer mRNA, the short interfering ribonucleic acid molecule is selected from the siRNAs described above along with at least one pharmaceutically acceptable carrier.

According to yet an additional aspect of the present invention there is provided a method of treating cancer in an individual, which includes inhibiting the expression of fer in cells or tissues of the individual.

According to further features in preferred embodiments of the invention described below, the method of treating cancer in an individual, which includes inhibiting the expression of fer in cells or tissues of the individual, includes inhibiting of expression of fer in cells or tissues of the individual being accomplished by degrading fer mRNA by providing a short interfering ribonucleic acid molecule being directed against fer mRNA, the short interfering ribonucleic acid molecule selected from the group consisting of the short interfering ribonucleic acid molecule described above.

According to still an additional aspect of the present invention there is provided a method of treating cancer in an individual animal, particularly a human, which includes inhibiting the expression of a gene in cells or tissues of the individual, wherein the inhibiting of expression of the gene in cells or tissues of the individual is accomplished by degrading mRNA corresponding to the gene by providing a short interfering ribonucleic acid molecule being directed against the mRNA.

According to further features in preferred embodiments of the invention described below, the cancer or malignant tumor is a prostate cancer.

The present invention successfully addresses the shortcomings of the presently known configurations by providing methods and compositions for the diagnosis, prevention, and treatment of cancer in manuals, and in particular, humans. More particularly, the present invention provides methods and compositions for the diagnosis, prevention, and treatment of cancer through detection and modulation of the expression of TMF/ARA160 and Fer.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 2 is an immunocytochemical analysis, using the methods and compositions of the present invention, illustrating the subcellular localization of TMF/ARA160 in mammalian cells;

FIG. 3 is an immunocytochemical analysis, using the methods and compositions of the present invention, illustrating that TMF/ARA160 co-localizes with the Golgi in mammalian cells;

DESCRIPTION OF THE PREFERRED EMBODIMENTS

Figure 1:
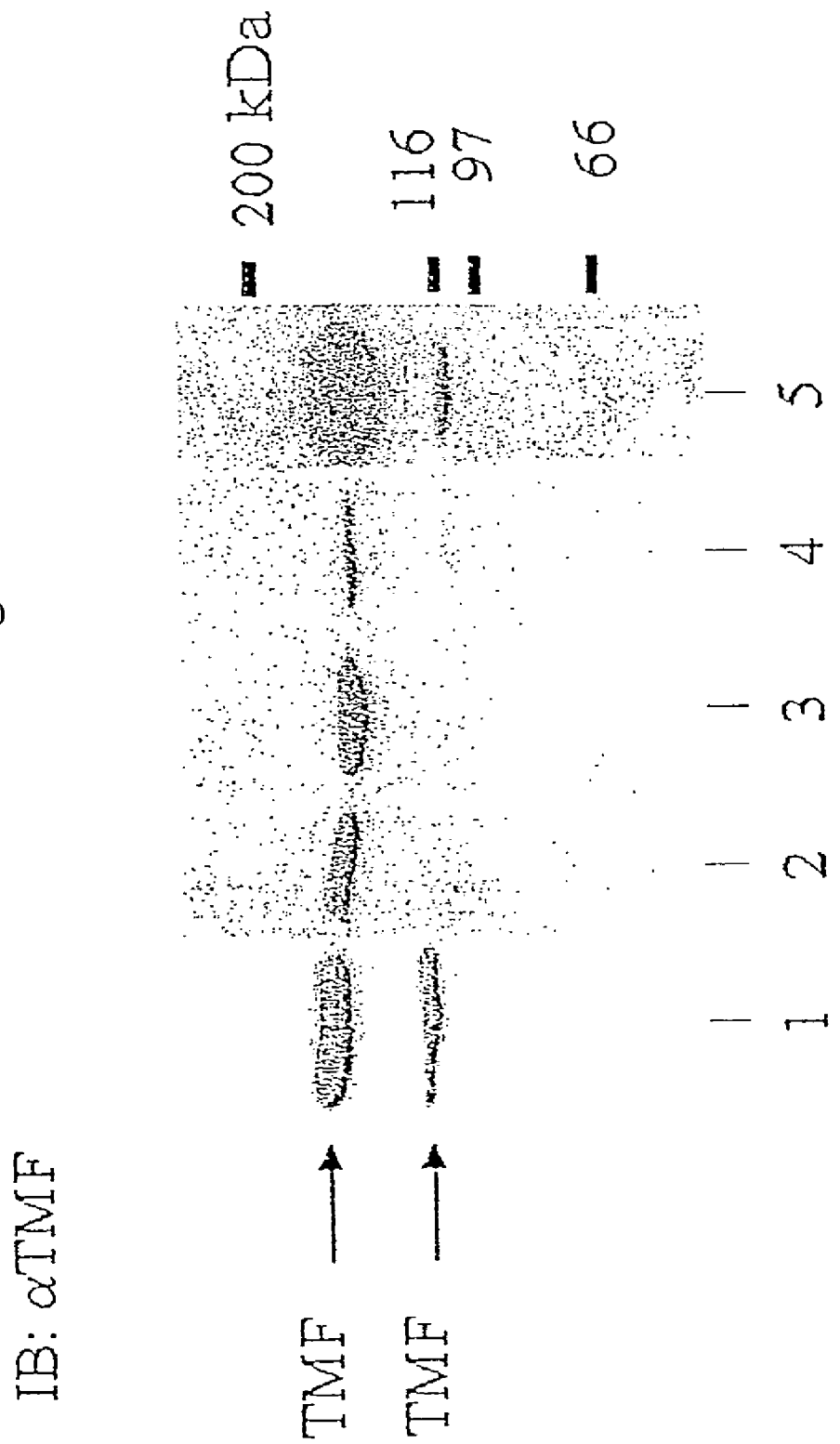
FIG. 1 is an immunoblot, using the methods and compositions of the present invention, demonstrating TMF/ARA160 protein in mammalian cell lines.

The present invention is of methods and compositions which can be used for the diagnosis, prevention, and treatment of cancer in mammals, and in particular, humans. Specifically, the present invention includes compositions and methods that can be used for diagnosing cancer by assessing the relative cellular levels of TMF/ARA160 in a biological sample. The present invention further includes methods and compositions that can be used for the prevention and treatment of cancer by increasing levels of TMF/ARA160, or reducing levels of fer, in cells and tissues.

The principles and operation of methods and compositions which can be used for the diagnosis, prevention, and treatment of cancer according to the present invention may be better understood with reference to the drawings and accompanying descriptions and examples detailed hereinunder.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

The present invention demonstrates (as shown in the examples hereinunder) that TMF/ARA160 serves also as a "Gate-Keeper", or GK, and it antagonizes the establishment of malignant state in mammalian cells. For the purposes of this specification and the accompanying claims, the terms TMF, ARA160, TMF/ARA160, Gate-Keeper, GK, and co-activator are used interchangeably. Further the terms FER tyrosine kinase, FER, and p94fer are also used interchangeably. Consequently, GK interferes with cancer progression and could thus be regarded as a tumor suppressor protein. It is demonstrated that one mechanism by which TMF/ARA160 antagonizes the uncontrolled growth of malignant cells is by recruiting key proliferation promoting factors like Stat3 and cyclin D1 to their degradation For the purposes of this specification and the accompanying claims, the terms cancer, malignancy, tumor, and malignant tumor are used interchangeably.

Considering these findings, it was predicted that the cellular effects of TMF/ARA160 are overridden in established cancer cells or that its function is neutralized in these cells. This could be achieved by antagonizing the activity of TMF/ARA160 or by abolishing its accumulation in cancer cells.

To further demonstrate the cellular role of TMF/ARA160 and to explore its possible link to Fer and Stat3, the subcellular distribution of TMF/ARA160 was determined and its interactions with other cellular proteins characterized. In the present invention we show that TMF/ARA160 is a constituent of a novel regulatory pathway that involves also Fer and Stat3 and is also involved in the modulation of mammalian cell-growth.

The present invention includes compositions and methods for diagnosing cancer by assessing the relative cellular levels of TMF/ARA160 in a biological sample. The present invention is directed toward a method of diagnosing cancer in an individual comprising the steps of obtaining a biological sample from an individual and deleting the level of TMF/ARA160 in the sample. The absence or low level of TMF/ARA160 in the sample is indicative of the presence of cancer in the sample. Preferably, the detection of the level of TMF/ARA160 utilizes antibody against TMF/ARA160. The present invention further features antibody against TMF/ARA160. The invention also encompasses kits for detecting the presence of TMF/ARA160 in a biological sample. The present invention further includes methods for the prevention and treatment of cancer by increasing levels of TMF/ARA160 in cells.

Antibodies used in the method of the invention, which can be intact antibodies or fragments thereof, can be polyclonal, or more preferably monoclonal. The antibody according to the present invention has a relatively-wide applicability to a variety of fields which require the detection of the polypeptide. When used in labeled immunoassays such as radioimmunoassay, enzyme immunoassay, and fluorescent immunoassay, the monoclonal antibody can qualitatively and quantitatively detect the polypeptide in samples instantly and accurately. In such assays, the monoclonal antibody is labeled, for example, with radioisotopes, enzymes and/or fluorescent substances prior to use. The antibody specifically reacts with the polypeptide to exhibit an immunoreaction, and accurately detects a slight amount of the polypeptide in samples by measuring the level of the immunoreaction for these labeled substances.

The antibodies can be labeled for ease of detection, i.e., directly labeled through coupling to a detectable substance (e.g., radioactive, enzymatic or fluorescent label) as well as indirectly labeled through reaction with another reagent that is directly labeled. Examples of indirect labeling include, for example, detection of a primary antibody using a fluorescently labeled secondary antibody. In preferred embodiments, the antibodies, fragments or derivatives are incorporated into immunoconjugates consisting of an antibody molecule or binding region thereof coupled (i.e., physically linked) to a detectable substance. Examples of detectable substances include various enzymes, prosthetic groups, fluorescent materials, luminescent materials, radioactive materials metal ions detectable by nuclear magnetic resonance, or other tracer molecule can be made by techniques known in the art. For instance, examples of suitable enzymes include horseradish peroxidase, alkaline phosphatase, B-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate; rhodamine, dichlorotriazinylamine fluorescein, dansyl chloride or phycoerythrin; an example of a luminescent material includes luminol; and examples of suitable radioactive materials include $^{125}I$, $^{131}I$, $^{35}S$, or $^{3}H$.

The term "biological sample" is intended to include but not be limited to, any tissue, cells and biological fluids (including, but not limited to serum plasma, blood, lymph, cerebrospinal fluid, urine, fluid from body cavities such as the peritoneal space [ascites], pleural, pericardial, etc., cystic fluid, and exudates) isolated from a subject, including those obtained as surgical and biopsy samples, or from procedures such as washings of body cavities, as well as tissues, cells anal fluids present in vivo within the subject. Surgical and biopsy samples can be procured and samples stored under standard conditions to prevent degradation until the detection method can be performed. Such samples include preservation methods such as paraffination.

The detection methods of the invention can be used in immunohistochemical staining of tissue samples (also known as immunocytochemical analysis) in order to evaluate the abundance of TMF/ARA160, or used diagnostically, e.g., in immunoassays, as part of a clinical testing procedure. Such immunoassays include, but are not limited to, competitive and non-competitive assay systems using techniques such as radioimmunoassays, ELISA, "sandwich" immunoassays, precipitin reactions, gel diffusion precipitin reactions, immunoradiometric assays, agglutination assays, complement fixation assays, immunoradiometric assays, fluorescent immunoassays, protein A immunoassays, and immunoelectrophoretic assays, to name but a few.

Such measurements can be useful in predictive evaluations of the onset or progression of cancer. Likewise, the ability to monitor the level of this protein in an individual can allow determination of the efficacy of a given treatment regimen for an individual afflicted with such a disorder.

The invention also encompasses kits for detecting the presence of TMF/ARA160 in a biological sample (e.g., cells, tissue, surgical or biopsy specimens, plasma, serum, urine or other biological sample as defined above). The kits include at least one reagent for detecting the presence of TMF/ARA160 in a biological sample. For example, the kit can comprise a labeled or labelable antibody, fragment or derivative which is capable of detecting TMF/ARA160 in a biological sample; means for determining the amount of the protein in the sample; and means for comparing the amount of TMF/ARA160 in the sample with a standard (e.g., purified protein) or control sample of normal tissue. The kit may include suitable fluids such as buffers, one or more sample compartments, standard or control samples, and the like. The kit can be packaged in a suitable container, which can also include instructions for using the kit to detect TMF/ARA160.

Moreover, while the specific examples described herein are from a rabbit, this is not meant to be a limitation. The antibodies of the invention having the desired specificity, whether from a rabbit source, other mammalian source including mouse, rat, sheep, human, or other sources, or combinations thereof, are included within the scope of this invention.

The antibodies can be used for the detection and/or enumeration by indirect staining of cells and tissues in normal individuals or in disease states, for example, by fluorescence microscopy, flow cytometry, immunoperoxidase, or other indirect methodologies.

To analyze the relative cellular levels of TMF/ARA160 in normal and in malignant cells, specific antibodies against the TMF/ARA160 protein ($\alpha$TMF/ARA160) [$\alpha$ is used throughout to indicate anti-] are raised, which are used as an efficient analytical tool in the study of that factor. Examples One and Two hereinunder including FIGS. 1-7 and 8-11 give further details.

The findings described hereinunder in Examples 1 and 2, and in FIGS. 1-11, clearly demonstrate that the absence of TMF/ARA160 or its accumulation at relatively low levels, are directly linked to the onset or progression of the malignant state in mammalian cells. The existence of that phenomena in solid tumors which were derived from three different tissue, turns the impaired accumulation of TMF/ARA160 into a potential general marker for the onset or progression of cancer. The ability to detect TMF/ARA160 by using assays such as preferably either Western blot or immunohistochemical (see Example one,) analysis allows assessment of the level of TMF/ARA160, at the multi- and single cell levels, by applying the affinity purified $\alpha$TMF/ARA160 antibodies. This enables the reliable and simple test for early detection of cancer cells, for differentiating malignant from benign cells and for easy follow-up of tumor progression or regression, upon various cancer therapies TMF/ARA160 further serves as a predictive marker for envisaging the susceptibility of a given tumor to various therapeutic approaches. Moreover, the relative level of TMF/ARA160 serves as a prognostic tool with which one is able to assess the characteristics (growth rate, metastasis, etc.) of a given tumor. The potential application of the TMF/ARA160 marker is extremely beneficial in highly lethal cancers like pancreatic adenocarcinoma, where tumor specific markers are urgently needed.

Activation of the TMF/ARA160 System—The present invention further includes methods for the prevention and treatment of cancer by increasing levels of TMF/ARA160 in cells. Such increase in TMF/ARA160 level can be achieved by activation of the TMF/ARA160 gene or other methods that increase the levels of TMF/ARA160 protein in the cell. The invention features a method of treating cancer in a patient, e.g., a mammalian such as a human, by administering to the mammal a compound in an amount effective to increase the level of expression or activity of the to TMF/ARA160 gene transcript or TMF/ARA160 gene product to a level effective to treat the cancer. In this method the compound can be a nucleic acid whose administration results in an increase in the level of expression of the TMF/ARA160 gene thereby ameliorating symptoms of the cancer. In another aspect, the invention includes a method for inhibiting tumors in a mammal by administering to the mammal a normal allele of the TMF/ARA160 gene.

Activation of the TMF/ARA160 gene/protein in cancer cells leads to the downregulation of key proliferation promoting proteins, and to the subsequent growth arrest and death of the malignant cells. Enforced activation of the TMF/ARA160 gene/protein in cancer cells, is preferably achieved by using two main strategies: a) Activation of the endogenous TMF/ARA60 protein in cancer cells. Some signal-transduction pathways inactivate and downregulate the TMF/ARA160 protein in malignant cells. Some of the cellular enzymes which are involved in that inactivation process have been identified. At least one of these enzymes was found to play a pivotal role in the proliferation of cancer cells. However, the function of this enzyme is highly redundant in normal cells. Specific inhibiting approaches specifically interfere with the neutralizing activity of those enzymes, thus leading to the upregulation and activation of the TMF/ARA160. The end products are drugs that may be given systematically to patients and will interfere with cellular factors which downregulate TMF/ARA160. This will consequently lead to the upregulation and activation of TMF/ARA160 in cancer cells. b) The second strategy relies mainly on the enforced expression of an exogenous TMF/ARA160 protein in cancer cells. This goal is achieved by two main gene therapy approaches. One of them is viral and the other one is non viral. In the viral approach, the TMF/ARA160 cDNA (or a portion of the gene that directs the production of a normal TMF/ARA160 protein with TMF/ARA160 function) is cloned in viral vectors and the recombinant viruses carrying the TMF/ARA160 cDNA are introduced into tumors. Viral vectors include, but are not limited to adenovirus, adeno-associated virus and retrovirus vectors. This leads to the enforced expression of TMF/ARA160 in cancer cells and to the subsequent death of those cells. In the non viral approach, the TMF/ARA160 cDNA is "trapped" in synthetic, nano-particles (including, but not limited to, liposomes) which serve as vehicles for guided delivery of the TMF/ARA160 cDNA to cancer cells. The TMF/ARA160 cDNA is linked to an appropriate promoter of gene expression and will thus be active upon its penetration to the cells.

The present invention includes approaches for the enforced activation of TMF/ARA60 (Garcia, J. A. et al (1992) Proc. Natl. Acad Sci. USA 89:9372-9376; Hsiao, P.-W. and Chang, C. J. Biol. Chem. (1999) 274:22373-22379) in cancer cells. The first approach is based on the finding that serum starvation leads to the release of TMF/ARA160 from the Golgi of cells and to its subsequent activation in the cytoplasm (see Example One, hereinunder). Thus signal transduction factors seem to downregulate the activity of TMF/ARA160 Signaltransduction constituents which affect the activity of TMF/ARA160 have been identified. As a non-limiting example, the tyrosine kinase FER (p94fer) is one of the downregulators of TMF/ARA160. According to the present invention, specific inhibitors to p94fer for subsequent upregulation of TMF/ARA160, in cancer cells are utilized in the prevention or treatment of cancer. Moreover, Fer is essential for the proliferation of cancer cells independently of TMF/ARA160 (GK). Fer is highly expressed in all human cancers from both soft and solid tissues. Downregulation of Fer leads to growth of the growth arrest of prostate cancer cells, as illustrated hereinunder.

A) Developing Inhibitors Directed Toward the Tyrosine Kinase Domain of p94fer:

1) Combinatorial chemistry is adopted for developing inhibitors that bind the kinase domain of p94fer and consequently inhibit its kinase activity. Similar inhibitor-STI-571- of the oncogenic tyrosine kinase v-abl (which is causal of certain leukemias) was successfully applied in the treatment of certain human cancers (Marx, J. Science (2001) 292: 2231-2233). The drawback of that approach is that it is relatively difficult to get highly specific inhibitors, which lack side effects. Another, more specific approach is therefore applied in parallel.

2) Applying specific $p94^{fer}$ interfering approaches in malignant cells: Specific low-molecular weight drugs are preferred therapeutic agents in cancer therapy. New potential low-molecular weight molecule targets are identified that can specifically impair the kinase activity of $p94^{fer}$, in vivo.

The unique N-terminal tail of $p94^{fer}$ drives the oligomerization and autoactivation of the enzyme, in vivo (Orlovsky K, Ben-Dor I, Priel-Halachmi S, Malovany H. Nir U. Biochemistry 2000 39:11084-11091). This turns this segment into a potential target for specific, $p94^{fer}$ inhibitors. Three CC regions in the $p94^{fer}$ N-terminal tail, were found to mediate the oligomerization of the enzyme (Ben-Dor I, Bern O, Tennenbaum T, Nir U. Cell Growth Differ 1999;10:113-29; Craig A W, Zimgibl R, Greer P. J Biol Chem 1999;274:19934-42). Out of these, CCI (Craig A W, Zimgibl R, Greer P. J Biol Chem 1999;274:19934-42; Orlovsky K, Ben-Dor I, Priel-Halachmi S, Malovany H, Nir U. Biochemistry 2000 39:11084-11091) and CCII (Craig A W Zimgibl R. Greer P. J Biol Chem 1999;274:19934-42) were found to be essential for the oligomerization of $p94^{fer}$. Perturbing the structure of either one of these two subdomains, compromised the ability of $p94^{fer}$ to oligomerize, in vivo. Thus, CC domains I and II can serve as interference targets, for inhibiting the oligomerization and autophosphorylation of $p94^{fer}$, in vivo. To specifically interfere with the oligomerization of CCI and CCII, two 20 amino acids long polypeptides, one derived from the central region of CCI and the other one from CCII (Ben-Dor I, Bern O, Tennenbaum T, Nir U. Cell Growth Differ 1999;10: 113-29), are synthesized. These synthetic peptides interact and oligomerize with their corresponding, CC sequences in the endogenous $p94^{fer}$, thus interfering with the oligomerization and autophosphorylation of the kinase. Indeed a synthetic peptide directed toward CCI, was shown to interfere with the ability of that sub-domain to interact with other CC domains, in vivo (Arregui C, Pathre P, Lilien J, Balsamo J. J Cell Biol 2000;149:1263-74.) To increase the membrane permeability of the two peptides, they may be linked at their N-terminal ends to decanoic acid. This fatty acid was found to effectively assist peptides in crossing the cell membrane, thus avoiding the need for internalization peptide sequences that could affect the structure of the functional peptide sequence (Arregui C, Pathre P, Lilien J, Balsamo J. J Cell Biol 2000; 149:1263-74). To assess the penetration of the $p94^{fer}$ derived peptides, through the cell membrane, the modified peptides are biotinylated (Arregui C, Pathre P, Lilien J. Balsamo J. J Cell Biol 2000;149:1263-74) and incubated (50-100 μm) faith the malignant and non-malignant breast and prostate cell lines. The subcellular accumulation and localization of the biotinylated peptides is detected by using Fluorescein labeled Streptavidin in immunocytochemical analysis. As satisfactory permeability is achieved, malignant and non-malignant cells are incubated with the non-biotinylated peptide. The effect of the two synthetic peptides, on the inhibition of $p94^{fer}$ activity and the activation of TMF/ARA160 is determined in cancer cells treated with 50-100 μm of each of the peptides, for 24, 48 and 72 h. These analyzed parameters are compared to those obtained with a non-relevant 20 amino acid long peptide, derived from the most extreme N-terminal sequence of p94$^{fer}$. That region was not found to be involved in the oligomerization of the kinase (Orlovsky K, Ben-Dor I, Priel-Halachmi S, Malovany H, Nir U. Biochemistry 2000 39:11084-11091.)

This is the basis for the design of novel low-molecular weight molecules, derived from the tested synthetic peptides and which specifically interfere with the activity of p94$^{fer}$, in malignant cells.

RNA interference with siRNA: The present application also includes compositions, kits, and methods for the application of short interfering RNA (siRNA) directed toward the Fer mRNA to specifically degrade that mRNA and consequently downregulate the cellular level of the Fer protein.

Determining the function of a particular gene is central to understanding the genetic and molecular basis of disease. A particularly effective method for determining a gene's function is to inactivate, or knock-out, that gene and to then study the effect of that inactivation on the cell or organism. However, classical methods used for inactivation of a specific gene are time consuming, technically challenging, costly and in some cases ineffectual and not gene-specific. Recently, a new technique has been developed called RNA interference, or RNAi, which allows for the selective inactivation of a target gene in a highly specific and effective manner (Sharp, P. A. *Genes Dev* 15: 485-490, 2001; Hannon, G. J. *Nature* 418: 244-251, 2002; Fire, A. et al. *Nature* 391: 806-811, 1998). Introduction of double-stranded RNA (dsRNA) corresponding to the sequence of a targeted transcript into a cell causes the rapid destruction of the targeted gene's messenger RNA (containing the identical sequence to either of the RNA strands in the duplex) thus preventing the production of the protein encoded by that gene. RNA interference leads to the inhibition of protein expression by utilizing sequence-specific, dsRNA-mediated destruction of the target messenger RNA (mRNA). In mammalian cells, the use of long dsRNA (greater than 50 bp) has been limited because it also induces a non-specific inhibitory response as part of the interferon pathway, which results in a general inhibition of protein synthesis. Studies indicate this can be avoided by the use of short dsRNAs (of 21-23 bp) called short interfering RNAs (siR-NAs) (Caplen, N. J., Parrish, S., Imai, F., Fire, A. & Morgan, R. A. *Proc Natl Acad Sci USA* 98, 9742-9747, 2001; Elbashir, S. M., Lendeckel, W. and Tuschl, T. Genes Dev 15:188-200, 2001, Elbashir, S. M., Harborth, J., Lendeckel, W., Yalcin, A., Weber, K., and Tuschl, T. Nature 411:494-498, 2001; Brummelkamp, T. R., Bernards, R., and Aagami, R. *Science* 296: 550-553, 2002; Tuschl, T. *Nature Biotechnology* 20:446-448, 2002; Paul, C. P., Good, P. D, Winer, I., and Engelke, D. R. *Nature Biotechnology* 20:505-508, 2002). These siRNAs act catalytically at sub-molar ratios to cleave greater than 95% of the target mRNA in the cell by acting as guides for a cellular enzyme complex that destroys complementary RNA sequences. The RNA interference effect can be long-lasting and may be detectable after many cell divisions, down regulating gene expression in a sequence-specific manner. In nature, it is believed that RNAi acts as a natural defense against viral infection, and recent studies have explored its potential application in the control of viral infections such as HIV infection (Lee, N S., Dohjima, T., Bauer, G., et al. *Nature Biotechnology* 20:500-505, 2002; Skipper, M. *Nature Rev Gen* 3:572-572, 2002). siRNAs have been used heretofore as research reagents by those of ordinary skill in the art to elucidate the function of particular genes in cultured cells. The feasibility of their use in mice in vivo has been demonstrated for research purposes for studying gene function. The use of RNAi or siRNAs for the prevention or treatment of cancer has not heretofore been described or demonstrated.

The present application includes a method for the treatment of cancer using the administration of siRNA for modulating the expression of particular genes. Specifically, the present application includes compositions, kits, and methods for the application of short interfering USA (siRNA) directed toward the Fer mRNA to specifically degrade that mRNA and consequently downregulate the cellular level of the Fer protein. Use of such compositions and methods led to the growth arrest of prostate cancer cells in in vitro culture and to their subsequent death (see Example Three hereinunder). This provides the underlying basis for the application of the siRNA approach to the treatment of cancer in vivo in mammals (see Example Four hereinunder).

The method for the treatment of cancer using the administration of siRNA for modulating the expression of particular genes includes the delivery of siRNA duplexes into the tumor cells and tissues, as well as the surrounding tissues.

For the purposes of this specification and the accompany claims, siRNA is used to refer to RNA duplexes, generally 21-23 nucleotides in length, generally synthetic, which act to degrade mRNA sequences homologous to either of the RNA strands in the duplex.

A preferred embodiment of the method for the treatment of cancer using the administration of siRNA for modulating the expression of particular genes according to the present invention includes the selection of a gene to be targeted for silencing, by degradation of its corresponding mRNA, such that expression of that gene is inhibited. Genes appropriate for use include those known to be involved in cell growth and proliferation such as proliferation promoting factors, including cell cycle genes, a myriad of which are known (see Vogelstein, B, and Kinzler, K. W., *The Genetic Basis of Human Cancer McGraw Hill*, 2002 for examples). In a preferred embodiment of the method of the present invention the gene for fer is chosen for targeting as illustrated below in the examples. Alternate genes include those for cell cycle control genes such as cdks and cyclins as non-limiting examples.

The method further includes the step of selecting a target sequence in the target mRNA and design of the siRNA duplexes for the target mRNA. Target sequence selection and siRNA duplex design is based on the guidelines of Tuschl et al., as have become standard in the art (Tuschl, T., P. D. Zamore, R. Lehmann, D. P. Bartel and P. A Sharp *Genes Dev* 13: 3191-3197 (1999); The siRNA user guide [http://www-.mpibpc.gwdg.de/abteilungen/100/105/sima.html]; Elbashir S M, Harborth J, Weber K, Tuschl T. *Methods* Feb; 26(2):199-213, (2002); Technical Bulletin #003-Revision B, Dharmacon Research, Inc. Lafayette, Colo., 2002).

The most efficient silencing is obtained with siRNA duplexes composed of 21-nt sense and 21-nt antisense strands, paired in a manner to have a 19-nucleotide duplex region and a 2-nt 3' overhang, (of preferably either UU or dTdT) at each 3' terminus. Symmetric 3'-overhangs ensure that the sequence-specific endonuclease complexes (siRNPs) are formed with approximately equal ratios of sense and antisense target RNA cleaving siRNPs. The 3'-overhang in the sense strand provides no contribution to recognition as it is believed the antisense siRNA strand guides target recognition. Therefore, the UU or dTdT 3'-overhang of the antisense sequences is complementary to the target mRNA but the symmetrical UU or dTdT 3'-overhang of the sense siRNA oligo does not need to correspond to the mRNA. The use of deoxythymidines in both 3'-overhangs may increase nuclease resistance, although siRNA duplexes with either UU or dTdT overhangs work equally well. 2'-Deoxynucleotides in the 3' overhangs are as efficient as ribonucleotides, but are often cheaper to synthesize.

The targeted region in the mRNA, and hence the sequence in the siRNA duplex, are chosen using the following guidelines. The open reading frame (ORF) region from the cDNA sequence is recommended for targeting, preferably at least 50 to 100 nucleotides downstream of the start codon, most preferably at least 75-100. Both the 5' and 3' untranslated regions (UTRs) and regions near the start codon are not recommended for targeting as these may be richer in regulatory protein binding sites. UTR-binding proteins and/or translation initiation complexes may interfere with binding of the siRNP endonuclease complex.

The sequence of the mRNA or cDNA is searched seeking the sequence AA(N19)TT. Sequences with approximately 50% G/C-content (30% to 70%) are used. If no suitable sequences are found, the search is extended to sequences AA(N21). The sequence of the sense siRNA corresponds to 5'-(N19)dTdT-3' or N21, respectively. In the latter case, the 3' end of the sense siRNA is converted to dTdT. The rationale for this sequence conversion is to generate a symmetric duplex with respect to the sequence composition of the sense and antisense 3' overhangs. It is believed that symmetric 3' overhangs help to ensure that the siRNPs are formed with approximately equal ratios of sense and antisense target RNA-cleaving siRNPs. The modification of the overhang of the sense sequence of the siRNA duplex is not expected to affect targeted mRNA recognition, as the antisense siRNA strand glides target recognition.

If the target mRNA does not contain a suitable AA(N21) sequence, it is recommended to search for NA(N21) The sequence of the sense and antisense strand may still be synthesized as 5' (N19)TT as the sequence of the 3' most nucleotide of the antisense siRNA does not appear to contribute to specificity.

It is further recommended to search the selected siRNA sequence against EST libraries in appropriate databases (e.g., NCBI BLAST database search) to ensure that only one gene is targeted.

At least one siRNA duplex is used. Although siRNA silencing appears to be extremely effective by selecting a single target in the mRNA, it is preferable to design and employ two independent siRNA duplexes to control for specificity of the silencing effect. Studies on the specificity of target recognition by siRNA duplexes indicate that a single point mutation located in the paired region of an siRNA duplex is sufficient to abolish target mRNA degradation.

The appropriately designed siRNAs are either obtained from commercial sources (such as Dharmacon Research, Lafayette, Colo.; Xergon, Huntsville, Ala.; Ambion, Austin, Tex.) or chemically synthesized used appropriately protected ribonucleoside phosphoramidites and a conventional DNA/RNA synthesizer according to standard protocols. The RNA oligonucleotides are fusser 2' deprotected, desalted and the two strands annealed, according to manufacturer's specifications or conventional protocols, depending on how the siRNAs are obtained. All handling steps are conducted under strict sterile, RNase-free conditions.

The siRNAs are delivered in various manners, using a transfection carrier medium such as a liposome, cationic lipid medium, polyamine, polymer-lipid formulation, receptor targeted molecule, or other suitable transfection reagent. Such reagents are commercially available (e.g.: TransIT-TKO™, Mirus, Madison, Wis.; Metafectene™, Biontex, Munich, Germany; TransIT-In Vivo™, Mirus, Madison, Wis.; and, Oligofectamine™, Invitrogen, Carlsbad, Calif.) and use for transfection is according to manufacturers' specifications and instructions for preparation of siRNA-complex formation, as well as standardized protocols (e.g. Elbashir S M, Harborth J, Weber K, Tuschl T. *Methods* Feb. 96(2):199-213, (2002)). Variables such as time and manner of formulation of siRNA-carrier complexes is dependent on the specific reagents used and conditions are optimized for the transfection. Variables optimized include, as non-limiting examples, method of mixing (inversion vs. vortexing), formation of complexes in serum-free medium, and optimum reagent and siRNA concentrations.

The transfection reagent may further be a component of a pharmaceutical formulation or preparation for oral, rectal, ophthalmic, topical (including to mucous membranes), or parenteral administration for assistance in uptake, distribution, absorption and/or delivery of the siRNA. Such preparations may further be used for administration to the respiratory tract by inhalation or insufflation, to the lungs or via intratracheal, or intranasal delivery Topical delivery further includes epidermal and transdermal administration. Parenteral administration includes intravenous, intrarterial, subcutaneous, intraperitoneal, intracranial, or intramuscular injection or infusion including direct injection into tumor tissue. Pharmaceutical compositions and formulations may contain standard pharmaceutically suitable additional components including bases, diluents, thickeners, buffers, emulsifiers, and other suitable additives such as are standard in the art, including, but not limited to penetration enhancers, stabilizers, carrier compounds and other carriers or exipients. A representative United States patent that teaches pharmaceutical compositions and formulations for delivery and transfection of oligonucleotides includes, but is not limited to U.S. Pat. No. 6,426,221, which along with the references contained therein is herein incorporated by reference.

In alternative embodiments siRNA transfer is accomplished ex vivo or in vivo using other methods including electroporation, microinjection, or using specifically designed plasmids, expression constructs, or other viral and non-viral vectors. Specifically envisaged as being within the scope of the invention is the use of viral and non-viral vectors for delivery of the siRNA to specific target cells and tissues.

The siRNA is administered to cells and tissues (e g., tumors) either directly (by injection or topical application, as non-limiting examples) [see Example Four] or by means (intravenous administration, as a non-limiting example) such that the siRNA will be delivered to the tumor site. Gene silencing has been demonstrated in mouse liver cells after siRNA injection into mouse liver in vivo (McCaffrey A P, Meuse L, Pham T-T, Conklin D S, Hannon G J, and Kay M A. *Nature* 418:38-39, (2002)) and siRNAs have been demonstrated to be delivered to organs of adult mice after intramuscular and intravenous injection (Lewis D L, Hagstrom J E, Loomis A G, Wolff J A, Herweijer H. Efficient delivery of siRNA for inhibition of gene expression in postnatal mice. *Nat Genet* epublication ahead of print; doi:10.1038/ng944, 2002).

The present invention further includes specific oligonucleotides and siRNA duplexes directed against fer mRNA for use according to the methods of the present invention in the treatment of cancerous tumors (such as prostate cancer as a non-limiting example) as well as pharmaceutical and other compositions comprising the oligonucleotides and siRNA duplexes and kits including said siRNA oligonucleotides. (see Examples three and four).

Antisense oligonucleotides: Alternatively, another approach is used in an alternative preferred embodiment of the present invention for the targeted degradation of the Fer mRNA. Synthetic modified antisense deoxy-oligonucleotides, which are directed toward defined complementary sequences in the Fer mRNA are designed and introduced to cancer cells. These modified oligo-nucleotides include phosphothioate and/or methylphosphonate modified deoxy-nucleotides and lead to the degradation of the Fer mRNA sod consequently to the downregulation of the Fer protein. A representative United States patent that teaches compositions and methods for use of antisense oligonucleotides for the treatment of disease includes, but is not limited to, U.S. Pat. No. 6,426,221, which along with the references contained therein is herein incorporated by reference.

B) Introduction of the TMF/ARA160 cDNA into Cancer cells: Viral vectors (including, but not limited to retroviral vectors) are used to allow enforced, stable and long lasting expression of TMF/ARA160 in cancer cells. The retroviral vector used, is preferably a broad range vector (Coffin J. Varmus H E (Eds). Retroviruses. New York: Cold Spring Harbor Laboratory Press, 1996) into which the TMF/ARA160 cDNA (Garcia, JA. et al. (1992) Proc. Natl. Acad. Sci. USA 89:9372-9376; Hsiao, P. W. and Chang, C. J. Biol. Chem. (1999) 274:22373-22379), is transcribed under the control of the human cytomegalovirus (CMV) early promoter (like the pLNCX2 vector—CLONTECH).

Recombinant retroviruses which carry the TMF/ARA160 cDNA, are used to infect human cancer cells to enforce ectopic expression of TMF/ARA160 in the cells. This leads to the growth arrest of the infected cells. In a further method, the TMF/ARA160 cDNA is expressed tinder the control of specific promoters which drive the expression of tumor specific antigens. This restricts the accumulation of the ectopic TMF/ARA160 to cancer cells and avoids the damaging effect of the protein in non-malignant cells.

The present invention thus includes compositions, kits and methods for the improved diagnosis, prevention, and treatment of cancer.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques described above and below are those well known and commonly employed in the art Standard techniques are used for cloning, DNA and RNA isolation, amplification and purification Generally enzymatic reactions involving DNA ligase, DNA polymerase, restriction endonucleases and the like are performed according to the manufacturers specifications. These techniques and various other techniques are generally performed according to methods well known and standard in the art. Such techniques are thoroughly explained in the literature. See, for example, "Molecular Cloning: A Laboratory Manual" Sambrook et al., (1989); "Current Protocols in Molecular Biology" Volumes I-III Ausubel, R. M., ed (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,279,057; "Cell Biology: A Laboratory Handbook", Volumes I-III Cellis, J E, ed. (1994); "Culture of Animal Cells—A Manual of Basic Technique" by Freshney, Wiley-Liss, N. Y. (19941), Third Edition; "Current Protocols in Immunology" Volumes I-III Coligan J. E., ed. (1994); Stites et al. (eds), "Basic and Clinical Immnunology" (8th Edition), Appleton & Lange, Norwalk, Conn. (1994); Mishell and Shiigi (eds), "Selected Methods in Cellular Immunology", W. H. Freeman and Co., New York (1980); "Using Antibodies: A Laboratory Manual" (Ed Harlow, David Lane eds., Cold Spring Harbor Laboratory Press (1999)); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4.098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D, and Higgins S. J., eds. (1984); "Animal Cell Culture" Freshney, R. I., ed (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al, "Strategies for Protein Purification and Characterization—A Laboratory Course Manual" CSHL Press (1996); "The Genetic Basis of Human Cancer" Vogelstein, B, and Kinzler, K. W., McGraw Hill (2002); all of which are incorporated by reference as if fully set forth herein. Other general references are provided throughout this document. The procedures therein are believed to be well known in the art and are provided for the convenience of the reader. All the information contained therein is incorporated herein by reference.

Example One

TMF/ARA160 Associates with Fer, Cyclin D1 and Proteasome Degradable Stat3 in Serum Starved C2C12 Cells Abbreviations: WGA—Wheat germ hemagglutinin; FCS—Fetal calf serum; BFA—Brefeldin A; DMEM—Dulbecco's modified Eagle's medium; ELISA—Enzyme labeled immunoassay; PBS—Phosphate buffered saline.

Material and Methods

Cell lines C2C12 cells were grown in Dulbecco's modified Eagle's medium (DMEM) supplemented with 15% fetal calf serum (FCS) and 4% glucose. For growth arrest, cells were transferred to medium containing 0.5% FCS and 4% glucose. Starvation medium lacked serum but was supplemented with 4% glucose and 2 mM glutamine NIH3T3, COS1 and Hela cells were grown in DMEM containing 10% FCS MCF-7, PC-3 and MDA-MB-231 cells were grown in RPMI supplemented with 10% FCS, 1 mM sodium pyruvate and 2 mM glutamine Cells treated with proteasome inhibitor were exposed for 5 hr to 50 mM MG132, before being harvested.

Preparation of αTMF/ARA160 antibodies A cDNA fragment encoding amino acids 0-268, of the human TMF/

ARA160 (N-TMF/ARA160), was flanked by Sph1 and Xho1 sites and was inserted between the Sph1 and Sal1 sites in the pQE32, bacterial expression vector (Qiagen). In this vector the expressed protein is preceded at its N-terminus by six histidine residues and could thus be purified by immobilized metal affinity chromatography (IMAC). The TMF/ARA160 N-terminal fragment was expressed in E. coli JM109 cells and was then purified by IMAC, using TALON-metal affinity resin (Clontech) which consists on sepharose-cobalt beads. 200 mg of the purified TMF/ARA160 fragment were injected subcutaneously to 3 month old female rabbits. This was repeated two more times with 14 day intervals and the presence of αTMF/ARA160 antibodies in the obtained sera was determined using ELISA.

For Western blots (immunoblots) and immunocytochemical analysis, TMF/ARA160 anti-sera was affinity purified on a CNBr-activated sepharose (Pharmacia), to which 500 μg of histidine-tagged N-TMF/ARA160 antigen was covalently linked, according to the manufacturer (Pharmacia) instructions. The anti-serum (4 ml of the second bleeding) was passed three times through the column to allow the binding of αTMF/ARA160 antibodies to the N-TMF/ARA160 antigen. Non-relevant proteins were washed away with phosphate buffered saline (PBS) and the bound αTMF/ARA160 antibodies were eluted with 100 mM glycine buffer pH 2.5 (20 fractions, 0.25 ml each), followed by basic elution with 100 mM triethylamine pH 11.5 (20 fractions 0.25 ml each). Acidic fractions were neutralized with 1 M phosphate buffer pH 8 and basic fractions were neutralized with 1 M phosphate buffer pH 6.8. The titer and specificity of the αTMF/ARA160 antibodies in each factor were determined using Western blot analysis and were compared to the titer of the unpurified whole serum.

Immunocytochemical Analysis. Immunocytochemistry was carried out essentially as described before (Priel-Halachmi, S., Ben-Dor, I., Shpungin, S., Tennenbaum, T., Molavani, H., Bachrach, M., Salzberg, S. & Nir, U. (2000) J. Biol. Chem. 275, 28902-28910; Ben-Dor, I, Bern, O., Tennenbaum, T. & Nir, U. (1999) Cell Growth Differ. 10, 113-129) For TMF/ARA160 staining, cells were exposed to 1:150 diluted, affinity purified αTMF/ARA160 antibodies. The Golgi was stained with 1:1500 diluted fluorescein isothiocyanate-labeled wheat germ hemagglutinin (WGA) (Molecular Probes) or with 1:100 diluted αp58 rabbit polyclonal antibodies (Sigma). Rabbit polygonal antibodies were visualized with either fluorescein isothiocyanate conjugated, or Rhodamin conjugated, (1:200 diluted) donkey anti rabbit secondary antibodies. Nuclei were visualized by staining the DNA with 0.05 mg/ml propidium iodide or with 200 ng/ml solution of Hoechst nuclear dye. Bound fluorophors were detected with a Bio-Rad MRC 1024 upright confocal microscope with a krypton-argon ion laser Confocal microscope image analysis was performed using Bio-Rad software, and figures were compiled using the Laser Sharp 3.0 software package.

Western blot analysis. Whole cell protein extracts were prepared and 25 mg of each sample were resolved by 7% SDS-PAGE, as described before (Priel-Halachmi, S., Ben-Dor, I., Shpungin, S., Tennenbaum, T., Molavani, H., Bachrach. M., Salzberg S. & Nir, U. (2000) J. Biol. Chem. 275, 28902-28910). Electroblotted proteins were detected using polyclonal αTMF/ARA160 and αFer (Priel-Halachmi, S., Ben-Dor, I. Shpungin, S., Tennenbaum, T., Molavani, H., Bachrach, M., Salzberg, S. & Nir, U. (2000) J. Biol. Chem. 275, 28902-28910) antibodies; monoclonal αStat3, αStat1 and αcyclin D1 antibodies; and polyclonal αubiquitin antibodies (DAKO).

Immunoprecipitation. Immunoprecipitations were performed basically, as described before (Priel-Halachmi. S., Ben-Dor, I., Shpungin, S., Tennenbaum, T., Molavani, H., Bachrach, M, Salzberg, S. & Nir, U. (2000) J. Biol. Chem. 275, 28902-28910). In brief extracted proteins (750-1000 mg) were incubated overnight at 4 C with 1:50 affinity purified αTMF/ARA160 polyclonal antibodies. Antigen-antibody complexes were precipitated with protein A-Sepharose for 1 h at 4 C and were washed as described before (Priel-Halachmi, S., Ben-Dor, I., Shpungin, S., Tennenbaum, T., Molavani, H., Bachrach, M., Salzberg, S. & Nir, U. (2000) J. Biol Chem. 275, 28902-28910). Precipitated proteins were then resolved by SDS-PAGE, blotted onto nitrocellulose membranes, and reacted with polyclonal αFer, αubiquitin and αTMF/ARA160 antibodies, or monoclonal αStat1, αStat3 and αcyclin D1, antibodies.

Results

TMF/ARA160 accumulates in the Golgi of mammalian cells. To further characterize the cellular functions of TMF/ARA160, we have raised specific polyclonal antibodies, with which we could follow the subcellular localization and biochemical characteristics, of that protein. Referring now to the drawings, FIG. 1 illustrates the TMF/ARA160 protein in mammalian cell lines by immunoblotting (IB). Whole cell protein extracts from: NIH3T3 (1); PC-3 (2); MCF-7 (3); MDA-MB-231 (4) and C2C12 cells (5), were resolved by 7.5% SDS-PAGE. Proteins were blotted onto a nitrocellulose membrane and were then reacted with αTMF/ARA160 antibodies Migration distances of known protein markers, are shown on the right. Arrows on the left indicate TMF/ARA160. Antibodies raised against the first 200 amino acids of TMF/ARA160, specifically detected a 160 kDA protein in all cell lines analyzed (FIG. 1). However in extracts from C2C12 and NIH3T3 cells, additional 110 kDa protein could be seen (FIG. 1 lanes 1 and 5). The 110 kDa protein represent most probably a degradation product of the full size 160 kDa TMF/ARA160 protein (Hsiao, P. W. & Chang, C. (1999) J. Biol Chem. 274, 22373-22379).

To determine the subcellular distribution of TMF/ARA160, affinity purified antibodies were applied in an indirect immunocytochemical assay. FIG. 2 demonstrates the subcellular localization of TMF/ARA160 in mammalian cells. In FIG. 2A, COS1 cells were fixed and incubated faith: pre-immune serum (a); αTMF/ARA160 antibodies (b); and αTMF/ARA160 antibodies preincubated with the TMF/ARA160 immunizing antigen (c). Bound antibodies were visualized with Rhodamin-conjugated, donkey anti-rabbit antibodies. In FIG. 2B, C2C12 (a) and NIH3T3 cells (b) were fixed and stained with propidium iodide (red) and αTMF/ARA160 antibodies (green). Photographs represent confocal laser sections taken 1 μm apart. The original magnification of cells was 600×. Scale bars are in μm. Surprisingly, staining of COS1, NIH3T3 and the myogenic C2C12 cell line, revealed a tightly packed localization of TMF/ARA160, in a region that was juxtaposed to the nucleus (FIGS. 2A and B). This staining represented the TMF/ARA160 protein, since it could be competed away by a TMF/ARA160 derived polypeptide, toward which the antibodies were raised s (FIG. 2A [c]). The tightly packed, perinuclear localization of TMF/ARA160, resembled the localization of the Golgi apparatus, that overlaps the perinuclear localization of the microtubules organization center (moc) (FIG. 3B). To verify the localization of TMF/ARA160 to the Golgi, COS1 and Hela cells were subjected to double-stain, immunocytochemical analysis. The cells were co-stained with αTMF/ARA160 antibodies and a fluorescein-labeled WGA, that binds to sugar moieties in the distal face of the Golgi stack (Tartakoff, A. M. & Vassalli, P.

(1983) *J. Cell Biol* 97, 1243-1248). In parallel, the cells were co-stained with a specific Golgi marker- the p58 protein which is located on the microtubule-binding peripheral Golgi membrane (Bloom, G. S. & Brashear, T. A. (1989) *J. Biol. Chem.* 264, 160S3-16092). WGA and p58 staining overlapped the specific TMF/ARA160 staining in COS1 and in Hela cells, and all three stainings were restricted to a the same perinuclear spot in interphase cells (FIG. 3A and FIGS. 3B a, b and c). However, in mitotic cells TMF/ARA160 was co-dispersed with other Golgi components (data not shown) and was less compactly packed also in late diakinesis stages (FIG. 3Ba). Thus TMF/ARA160 is associated with or is stored in the Golgi organelle.

To further support this conclusion, the subcellular localization of TMF/ARA160, was followed in cells treated with the frugal metabolite, brefeldin A (BFA) that disrupts the Golgi apparatus by interfering with small G proteins required for its integrity (Reaves, B. & Banting, G. (1992) *J. Cell Biol.* 116, 85-94; Lippincott-Schwartz, J., Yuan, L.; Tipper, C, Amherdt, M., Orci, L & Klausner, R. D. (1991) *Cell* 67, 601-616; Robineau, S. Chabre, M. & Antonny, B. (2000) *Proc. Natl. Acad Sci U.S.A* 97, 9913-9918). FIG. 3 further demonstrates that TMF/ARA160 co-localizes with the Golgi in mammalian cells. In FIG. 3A, COS1 cells were fixed and stained with: αTMF/ARA antibodies (a) and WGA (b). The merged images of -a and b is illustrated in panel c. Cells were stained with propidium iodide (red) and αTMF/ARA160 antibodies (green) in panel d. In FIG. 3B, Hela cells were fixed and co-stained with: αtubulin (red) and αTMF/ARA160 (green) antibodies in panels (a) and (b); αp58 (red) and αTMF/ARA160 (green) antibodies in panel (c). BFA treated cells were fixed and co-stained faith αp58 (red) and αTMF/ARA160 antibodies (green) in panels (d) and (e). All nuclei were visualized with Hoechst (blue). The original magnification of the cells was 1000×. In cells exposed to BFA for 4 hr, both the p58 and the TMF/ARA160 staining were less packed and relatively dispersed in the cytoplasm (FIGS. 3B d and e). Thus disintegration of the Golgi leads to the release of TMF/ARA160 and its dispersion in the cytoplasm TMF/ARA160 was stored in the Golgi throughout most of the cell cycle stages, and was spread out only during mitosis, when the Golgi apparatus breaks down (data not shown).

TMF/ARA160 is released from the Golgi of serum deprived C2C12 cells. The accumulation of TMF/ARA160 in the Golgi, implies its exclusion from the cell cytoplasm and from the cell nucleus, thus preventing it from functioning as a putative transcription factor. TMF/ARA160 has been implicated previously as a general suppressor of genes transcribed by RNA polymerase II (RNA POL.II) (Garcia et al. 1992), and may thus be linked to impaired cell-growth. We therefore checked the subcellular distribution of TMF/ARA160, in growth arrested cells. Myogenic C2 C12) cells, were grown under both normal and low serum growth conditions, under the latter conditions, the cells undergo gradual differentiation and terminal growth arrest (Craig, A. W., Zirngibl, R., Williams, K., Cole, L. A & Greer, P. A. (2001) *Mol. Cell Biol* 21, 603-613). Cells were subjected to immunocytochemical analysis, before and after being transferred to 0.5% FCS, for 48 hr. These experiments were carried out with low serum rather than a complete lack of serum which led to some cell death, under the immunocytochemistry staining conditions.

Figure 4A:
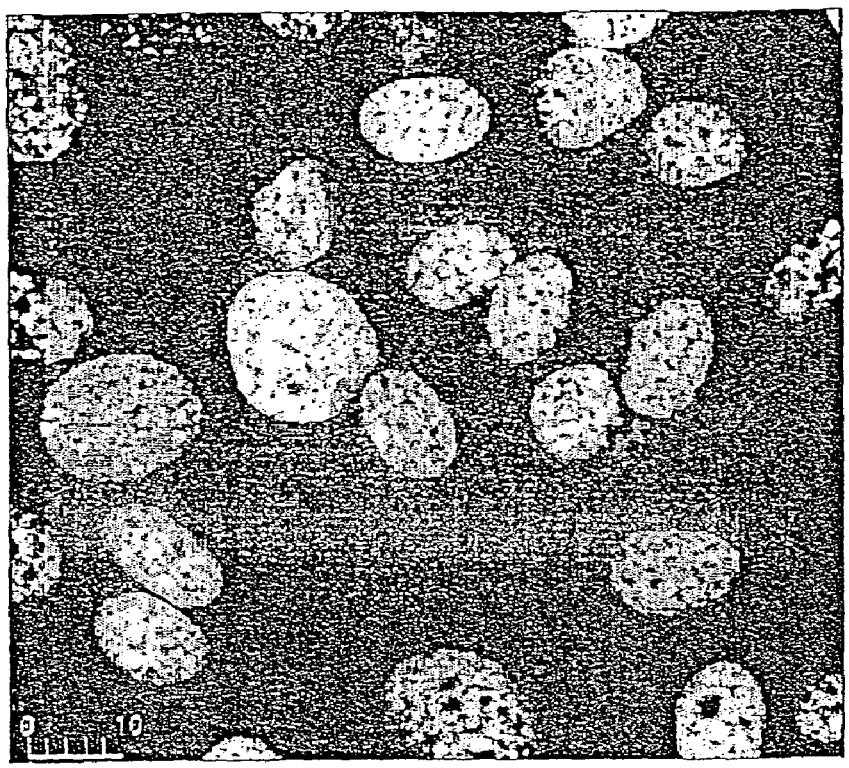
FIG. 4 is an immunocytochemical analysis, using the methods and compositions of the present invention, illustrating that TMF/ARA160 is released from the Golgi of serum starved C2C12 cells.
Figure 4B:
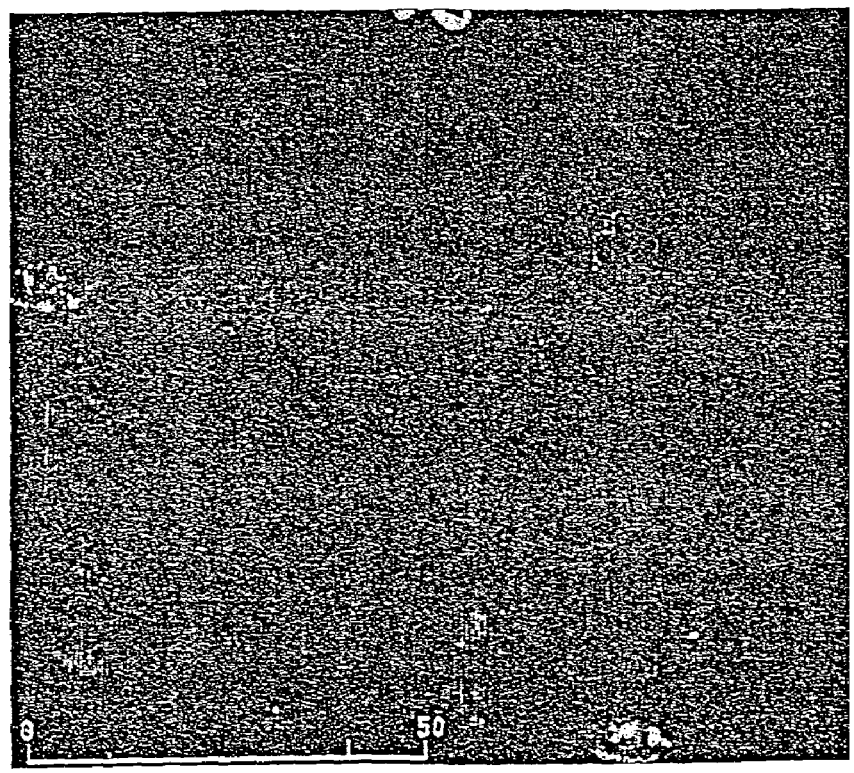

FIG. 4 shows that TMF/ARA160 is released from the Golgi of serum starved C2C12 cells. Actively grossing C2C12 cells (A) and cells grown under low serum growth conditions (B) were fixed and co-stained with αTMF/ARA160 (green) and propidium iodide (red). These photographs represent confocal laser sections taken 1 μm apart. The original magnification of cells was 600×. While being stored in the Golgi of actively growing cells, TMF/ARA160 was partially released from that organelle, in cells that were grown for 24 hr under low serum growth conditions (data not shown). TMF/ARA160 was further released from the Golgi and was almost fully spread throughout the cytoplasm, after 48 hr (FIG. 4). Low serum (0.5% FCS) growth conditions did not lead to the disintegration of the Golgi (data not shown), thus suggesting the specific release of TMF/ARA160 from the Golgi, under those conditions.

TMF/ARA160 associates with Fer in serum starved C2C12 cells. The release of TMF/ARA160 from the Golgi of serum starved cells, and its subsequent spreading in the cytoplasm, should enable the interaction of TMF/ARA160 with defined cytoplasmic factors. This process could lead to a newly activated function of TMF/ARA160, in growth arrested cells. One candidate protein that could potentially interact with TMF/ARA160 in the cytoplasm, is the tyrosine kinase Fer that vas shown to interact with TMF/ARA160, in a yeast two-hybrid screening system (Schwartz, Y., Ben-Dor, I., Navon, A., Motro, B. & Nir, U. (1998) *FEBS Lett.* 434, 339-345) and which is mainly cytoplasmic in both actively growing and in serum starved C2C12 cells. To test the possible association of these two proteins in-vivo, TMF/ARA160 was immunoprecipitated from non-starved and from serum deprived C2C12 cells by using affinity purified αTMF/ARA160, antibodies. This ensured specific precipitation of TNF/ARA160 and hence other proteins that were co-immunoprecipitated with it. Whole cell extracts were prepared from actively growing C2C12 cultures and from cells grown without serum for 24, 48 and 72 hr. αTMF/ARA160 immunoprecipitates were resolved by SDS-PAGE and were then subjected to αTMF/ARA160 and αFer antibodies in a Western blot analysis.

Figure 5:
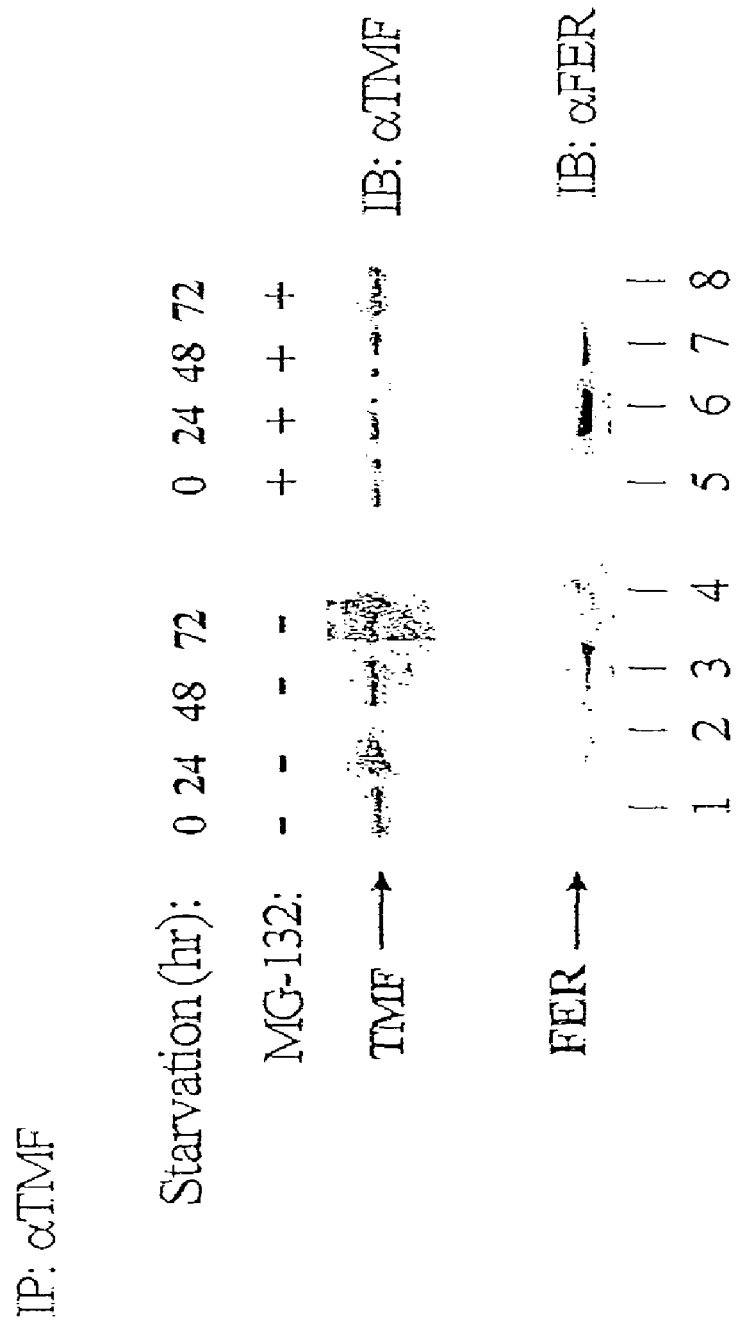
FIG. 5 is an immunoprecipitation, using the methods and compositions of the present invention, showing that TMF/ARA160 associates with Fer in serum starved C2C12 cells.
Figure 5:
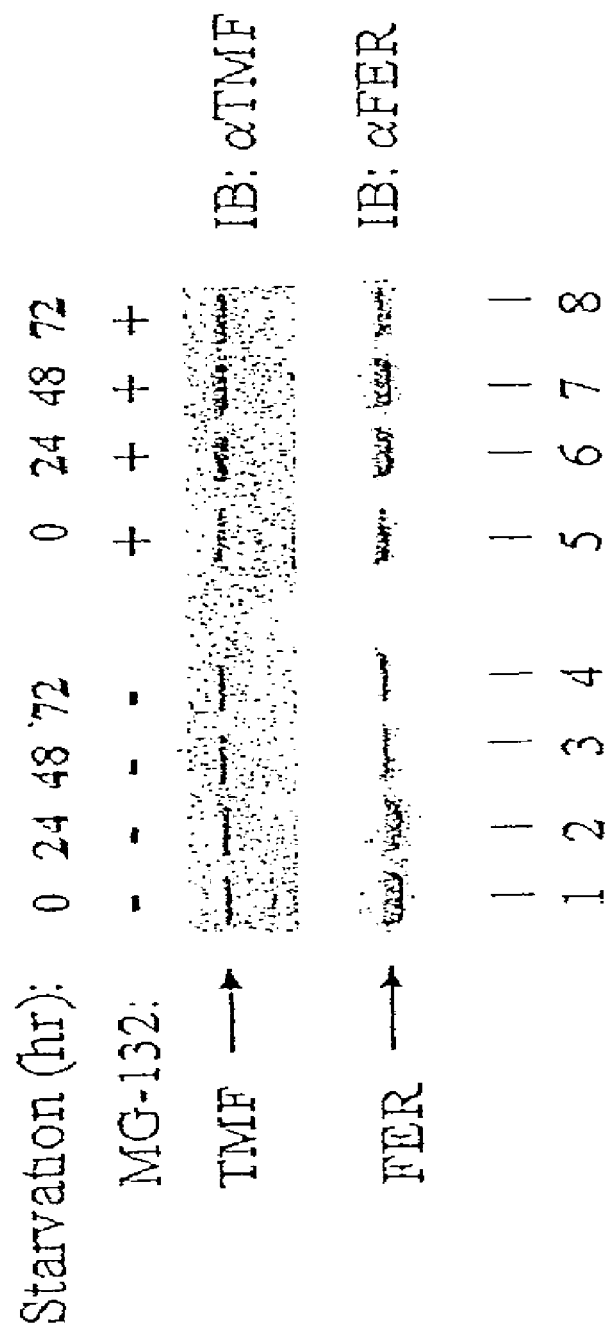

FIG. 5 is an immunoprecipitation (IP) showing that TMF/ARA160 associates with Fer in serum starved C2C12 cells. In FIG. 5A, whole cell protein extracts were prepared from actively growing (lanes 1 and 5) or serum deprived C2C12 cells (lanes 2-4 and 6-8) which were either untreated (lanes 1-4) or treated with MG132 (lanes 5-8). TMF/ARA160 was immunoprecipitated with affinity purified αTMF/ARA160 antibodies. Precipitates were resolved by 7% SDS-PAGE, blotted onto nitrocellulose membrane and reacted with αTMF/ARA160 (upper panel) or αFER antibodies (lower panel). B. Cellular levels of TMF/ARA160 and Fer, in serum starved C2C12 cells. Whole cell protein extracts were resolved by 7% SDS-OAGE and exposed in a Western-blot analysis to αTMF/ARA160 (upper panel) or αFER antibodies (lower panel).

TMF/ARA160 was immunoprecipitated from the different extracts with similar efficiency (FIG. 5A). However, obvious levels of co-immunoprecipitated Fer were detected only after 24 and 48 hr of serum starvation but not after 72 hr of serum starvation or in proliferating, non starved cells (FIG. 5A lanes 1-4). Thus the Fer kinase associates transiently with TMF/ARA160, in serum starved C2C12 cells Exposing the TMF/ARA160 immunoprecipitates, to antiphosphotyrosine antibodies (αPT), did not give any signal (data not shown), suggesting that the Fer fraction associated with TMF/ARA160, is not phosphorylated on tyrosine.

Since Fer seemed to be subjected to proteasomal degradation in serum starved C2C12 cells, immunoprecipitations were performed also from extracts of cells exposed to the proteasome inhibitor MG132. Fer associated transiently with TMF/ARA160 in these treated cells as well. However, the levels of the TMF/ARA160 associated Fer increased significantly in cells that were treated with MG132 (FIG. 5A lanes 6 and 7). The transient association of TMF/ARA160 and Fer, could reflect the changes in the accumulation levels of the two proteins, during the starvation process. We therefore determined the relative cellular levels of TMF/ARA160 and Fer, in actively growing and in serum starved C2C12 cells.

Western blot analysis of whole cell extracts, revealed that while the levels of TMF/ARA160 were mostly constant (FIG. 5B lanes 1-4) the Fer levels went down along the starvation process (FIG. 5B lanes 1-4). The decline in the Fer level was abolished in cells treated with the proteasome inhibitor MG132 (FIG. 5B lanes 5-8), suggesting that Fer is prone to proteasomal degradation, under those conditions. The transient association of Fer and TMF/ARA160 did not reflect, however, the cellular accumulation profiles of either one of these two proteins, suggesting that their association is a tightly controlled process.

Thus Fer seems to transiently associate with TMF/ARA160 before being directed to proteasomal degradation in serum-starved C2C12 cells.

TMF/ARA160 associates with proteasome degradable Stat3 and with cyclin D1 in serum starved C2C12 cells. The Fer kinase was shown previously to associate with Stat3 in C2C12 and in NIH3T3 cells (Priel-Halachmi, S., Ben-Dor, I., Shpungin, S., Tennenbaum, T., Molavani, H., Bachrach, M., Salzberg, S. & Nir, U. (2000) *J. Biol. Chem.* 275, 28902-28910). This raised the possibility that Stat3 also associates with the TMF/ARA160-Fer complex.

Figure 6:
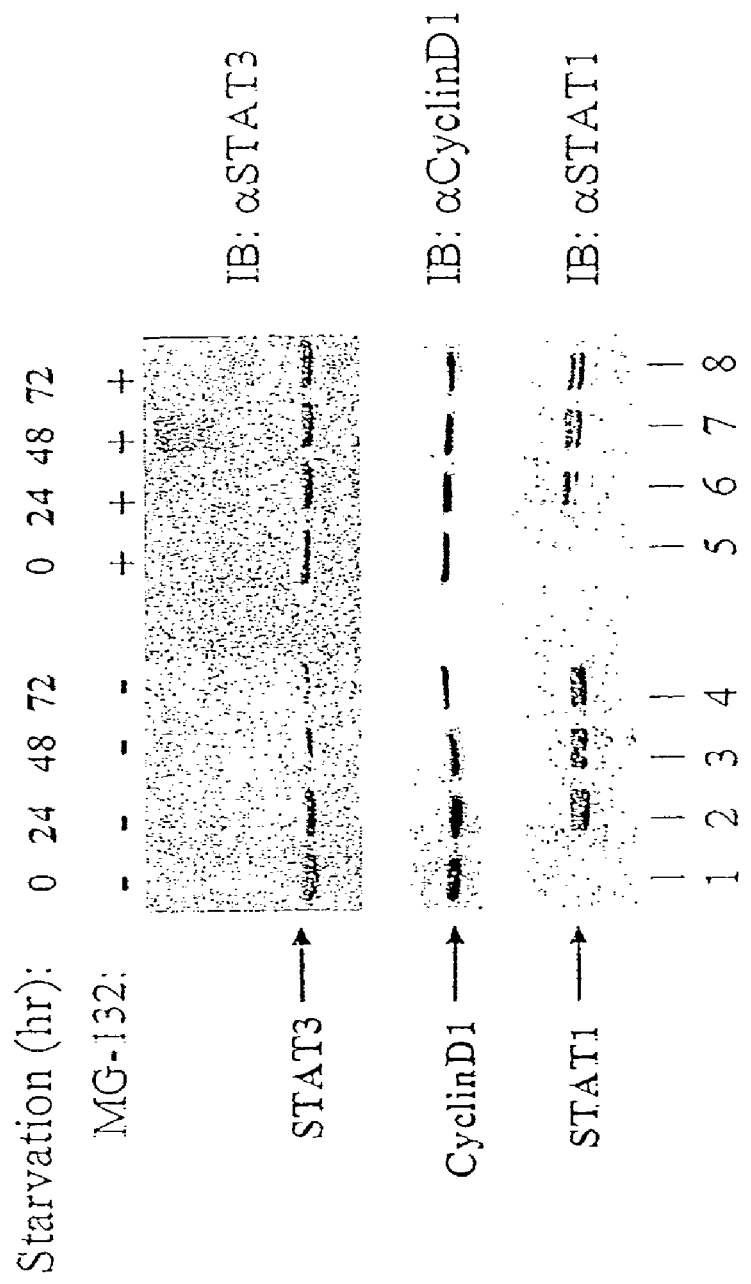
FIG. 6 is an immunoprecipitation, using the methods and compositions of the present invention, showing that TMF/ARA160 associates with cyclin D1 and Stat3 but not with Stat1, in serum starved C2C12 cells.
Figure 6:
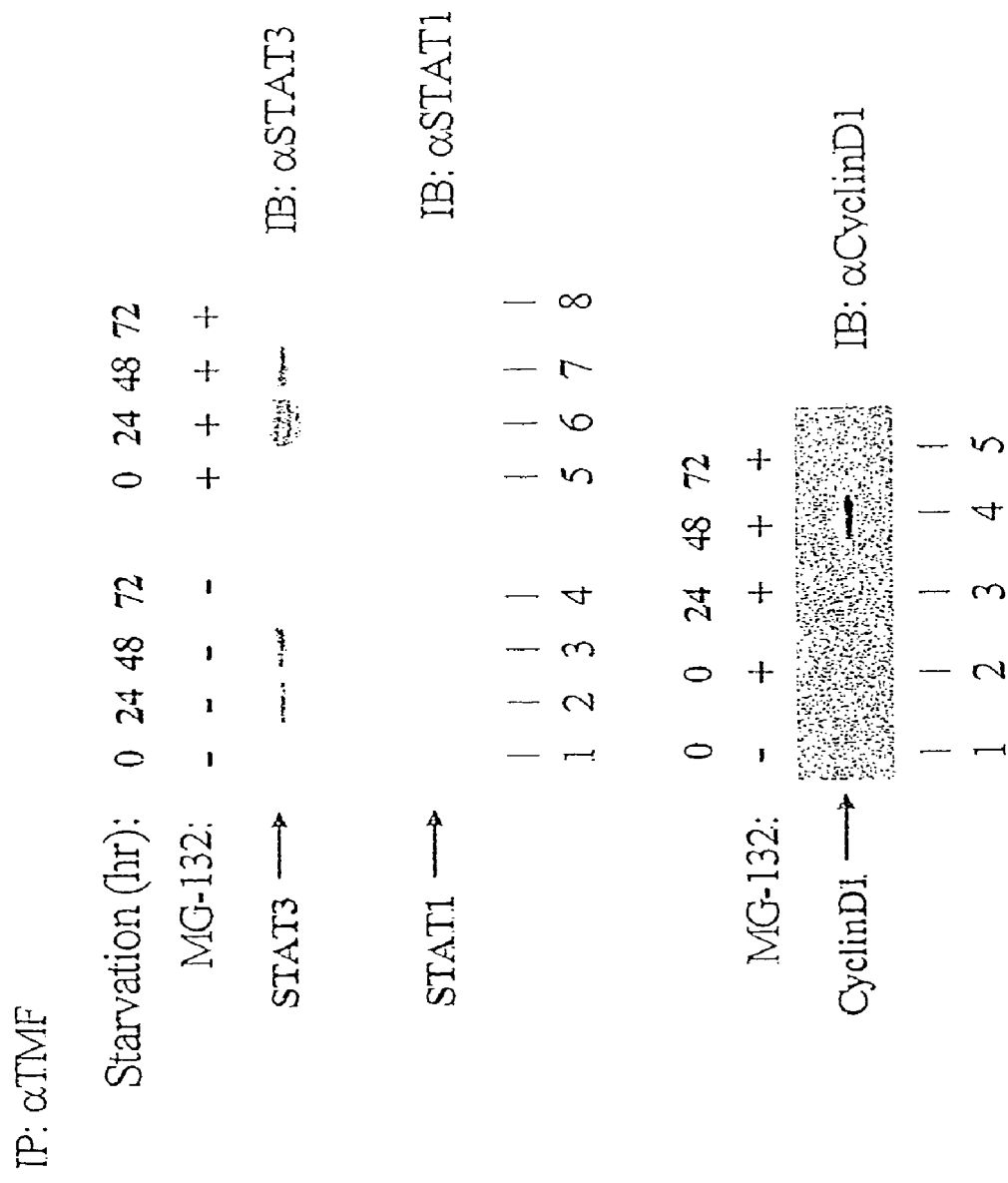

FIG. 6 is an immunoprecipitation showing that TMF/ARA160 associates with cyclin D1 and Stat3 but not with Stat1, in serum starved C2C12 cells. FIG. 6A shows cellular levels of Stat3, cyclin D1 and Stat1, in serum starved C2C12 cells. Whole cell extracts from actively growing (lanes 1 and 5) or serum-starved cells (lanes 2-4 and 6-8) which were either untreated (lanes 1-4) or treated with MG132 (lanes 5-8), were resolved by 7% SDS-PAGE and exposed to αStat3 (upper panel); αcyclin D1 (middle panel); or αStat1 antibodies (lower panel), in a Western-blot analysis. FIG. 6B shows that TMF/ARA160 co-immunoprecipitates with Stat3 and cyclin D1 but not with Stat1. TMF/ARA160 was immunoprecipitated from the extracts described in A. Precipitates were resolved by 7% SDS-PAGE and were reacted with αStat3 (upper panel); αStat1 (middle panel); or αcyclin D1 antibodies (lower panel), in a Western-blot analysis.

Western blot analysis revealed that the accumulation levels of Stat3 paralleled the expression profile of Fer, and declined progressively in serum starved C2C12 cells (FIG. 6A lanes 1-4) This decline was not seen in cells exposed to the proteasome inhibitor MG132 (FIG. 6A lanes 5-8), indicating that Stat3 is prone to post-translational degradation in the starved cells Moreover, high molecular weight forms of Stat3, which could represent ubiquitinated Stat3, were detected after 48 hr of serum starvation (FIG. 6A lanes 6 and 7).

To reveal whether Stat3 associates with TMF/ARA160, proteins precipitated with αTMF/ARA160 antibodies were resolved in SDS-PAGE and were then reacted with αStat3 antibodies, in a Western blot analysis. As was seen for the tyrosine kinase Fer, Stat3 did not associate with TMF/ARA160 in actively growing, non-starved cells (FIG. 6B lane 1 and 5). However, after 24 and 48 hr of serum starvation, Stat3 associated transiently with TMF/ARA160 and this association was barely seen after 72 hr of serum starvation (FIG. 6B lanes 4 and 8). The transient association of these two proteins increased significantly in cells treated with MG132, thus suggesting that Stat3 transiently associates with TMF/ARA160, before being destined to proteasomal degradation.

No signal was obtained when the TMF/ARA160-Stat3 immunoprecipitates were challenged with αPT, suggesting that the Stat3 associated with TMF/ARA160 is not phosphorylated on tyrosine To assess the specificity of the interaction between TMF/ARA160 and Stat3, the association of TMF/ARA160 with Stat1 vas analyzed as well. Unlike Stat3 which in many systems is implicated in the promotion of cell proliferation (Bromberg, J. F., Wrzeszczynska, M. H., Devgan, G., Zhao, Y., Pestell, R. G., Albanese, C. & Darnell, J. E., Jr. (1999) *Cell* 98, 295-303; Sinibaldi, D., Wharton, W., Turkson, J., Bowman, T., Pledger, W. J. & Jove, R. (2000) *Oncogene* 19, 5419-5427), Stat1 is linked mainly to impaired cell growth (Zhou, Y., Wang, S., Gobl, A. & Oberg, K. (2001) *Oncology* 60, 330-338). In accordance with that notion, the cellular levels of Stat1 increased gradually in C2C12 serum starved cells (FIG. 6A lanes 1-8). Exposing the TMF/ARA160 immunoprecipitates to αStat1 antibodies in a Western blot analysis, did not reveal any association of Stat1 with TMF/ARA160 in proliferating or in serum starved C2C12 cells (FIG. 6B lanes 1-8) This proved the specificity of the interaction between TMF/ARA160 and Stat3 or Fer, which are linked to the proliferation of mammalian cells.

To test whether other growth promoting factors could bind to TMF/ARA160, the association of TMF/ARA160 with cyclin D1 (Sinibaldi, D., Wharton, W., Turkson, J., Bowman, T., Pledger, W. J. & Jove, R. (2000) *Oncogene* 19, 5419-5427) was analyzed in serum-starved, C2C12 cells. As was seen for Stat3, TMF/ARA160 associated with cyclin D1 only at 24 and 48 hr post starvation, in MG132 treated cells (FIG. 6B lane 4, bottom panel). The cellular level of cyclin D1 was only moderately changing during C2C12 starvation (FIG. 6A lanes 1-4). Thus TMF/ARA160 binds preferentially to proliferation-related factors, in serum-starved C2C12 cells.

Cytoplasmic TMF/ARA160 associates with ubiquitinated proteins in C2C12 cells. The association of TMF/ARA160 with proteasome degradable Stat3, suggested the possible involvement of TMF/ARA160 in the exposure of Stat3 to proteasomal degradation. To confirm the direct link of TMF/ARA160 to ubiquitin dependent protein degradation, the association of ubiquitinated proteins with TMF/ARA160 was assessed. TMF/ARA160 was immunoprecipitated from both actively growing and serum-stared C2C12 cells and the precipitated proteins were resolved by SDS-PAGE.

Figure 7:
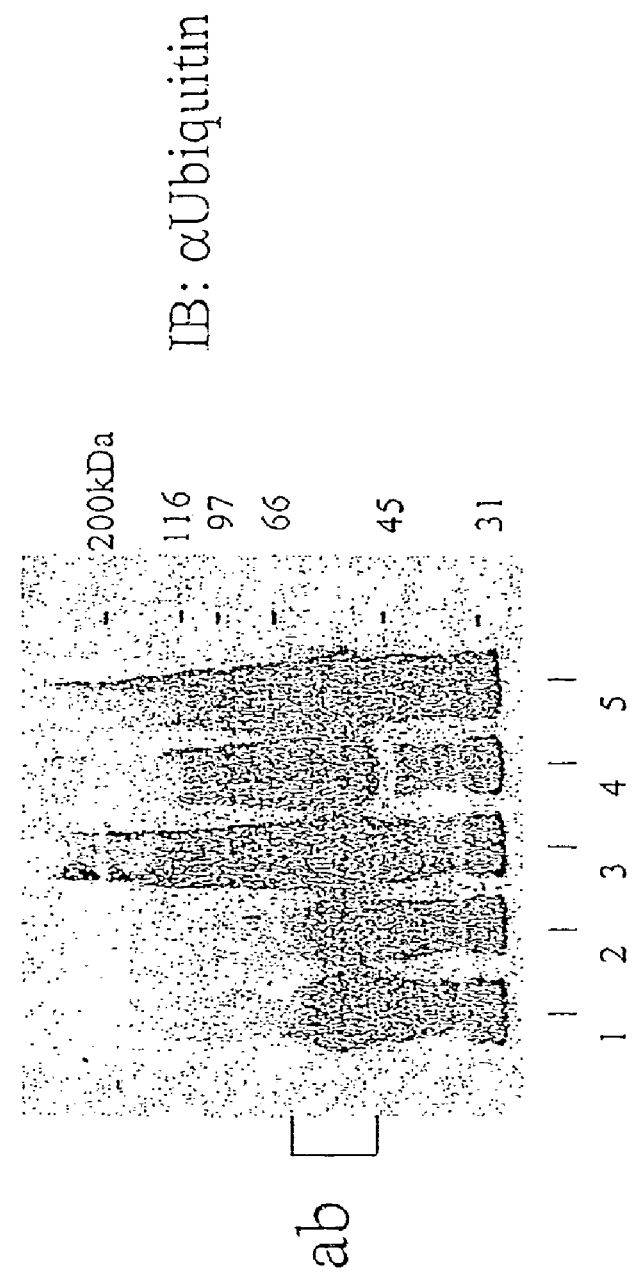
FIG. 7 is an immunoprecipitation using the methods and compositions of the present invention, demonstrating that unbiquitinated proteins associate with TMF/ARA160 in serum starved C2C12 cells.

FIG. 7 is an immunoprecipitation demonstrating that ubiquitinated proteins associate with TMF/ARA160 in serum starved C2C12 cells. TMF/ARA160 was immunoprecipitated from whole cell protein extracts of actively grossing (1) or serum starved (2-4) C2C12 cells. Precipitates were resolved by 7% SDS-PAGE and were reacted with αubiquitin antibodies in a Western-blot analysis. Migration distances of known molecular weight markers are given on the right. IP: immunoprecipitation; IB: immunoblotting; ab: location of the immunoprecipitating antibodies.

Western blot analysis carried out with αubiquitin antibodies, revealed the association of ubiquitinated proteins with the TMF/ARA160. This could be seen already in precipitates from actively growing C2C12 cells (FIG. 7 lane 1). However a prominent band of an approximate 90 kDa molecular mass could be clearly seen after 24 hr of serum starvation (FIG. 7 lane 2). This band disappeared after 48 and 72 hr of serum starvation (FIG. 7 lanes 3 and 4). The estimated size of the ubiquitinated protein (90 kDa), suggests that it does not represent ubiquitinated-TMF/ARA160 species, since ubiquitinated-TMF/ARA160, should migrate as a minimal 160 kDA protein in SDS-PAGE. It is most plausible therefore that the ubiquitinated 90 kDa band, reflects the transient association of TMF zenith another protein.

TMF/ARA160 is a putative transcription factor and co-activator of nuclear receptors (Garcia, J. A., Ou, S. H. Wu, F., Lusis, A. J., Sparkes, R. S. & Gaynor, R. B. (1992) *Proc. Natl. Acad. Sci. USA* 89, 9372-9376), whose physiological role has not been conclusively revealed Here we show, that the subcellular localization of TMF/ARA160 is unique and very uncommon for a transcription o TMF/ARA160 co-localized with WGA binding sites in the Golgi, suggesting the accumulation of TMF/ARA160 in that organelle. Confinement of TMF/ARA160 to the Golgi should exclude that protein from other cellular compartments and components. Furthermore, storage in the Golgi should prevent TMF/ARA160 from interacting with nuclear receptors and from migrating as their putative co-activator (Hsiao, P. W. & Chang, C. (1999) *J. Biol. Chem.* 274, 22373-22379) to the nucleus. One would argue that activators of nuclear receptors such as, glucocorticoids and androgens, could induce the release of TMF/ARA160 from the Golgi, thus leading to its spreading throughout the cytoplasm and its subsequent association with nuclear receptors. However, we failed to see any effect of dexamethasone on the subcellular distribution of TMF/ARA160 in C2C12 cells. TMF/ARA160 was released from the Golgi and was spread throughout the cytoplasm, in serum-stained cells. This suggests that signal transduction pathways induced by growth factor stimulation, drive the occlusion of TMF/ARA160 in the Golgi. Removal of growth factors from the surrounding of the cells leads therefore to the release of TMF/ARA160 to the cytoplasm. Thus, release of TMF/ARA160 from the Golgi, may be linked to cessation of cell growth.

Spreading of TMF/ARA160 throughout the cytoplasm of C2C12 cells results in its association with several cytoplasmic proteins that were identified in the current work. These include the tyrosine kinase Fer, cyclin D1 and Stat3. The association of Stat3 faith TMF/ARA160, could be mediated by Fer, since Stat3 was previously shown to associate with Fer in-vivo (Priel-Halachmi, S-, Ben-Dor, I, Shpungin. S., Tennenbaum, T., Molavani, H., Bachrach, M., Salzberg, S. & Nir, U. (2000) *J. Biol. Chem.* 275, 28902-28910) and Fer was shown to interact directly with TMF/ARA160, in a yeast two-hybrid screening system (Schwartz, Y., Ben-Dor, I, Navon, A., Motro, B. & Nir, U. (1998) *FEBS Lett.* 434, 339-345) Similarly, the association of Stat3 or cyclin D1 with TMF/ARA160, could also depend on the mutual interaction of these two factors, which were shown to bind each other, before (Bienvenu, F., Gascan, H. & Coqueret, O. (2001) *J. Biol. Chem.* 276, 16840-16847). However, the association of Stat3 with TMF/ARA160 does not seem to depend on Fer or on cyclin D1, since TMF/ARA160 associated with Stat3 but not with cyclin D1, in the thymoma derived T127 cells, that lack the Fer kinase (Halachmy, S., Bern, O., Schreiber, L., Carmel, M., Sharabi, Y., Shoham, J. & Nir, U. (1997) *Oncogene* 14, 2871-2880) Thus, Stat3, Fer and cyclin D1 bind TMF/ARA160 either directly or through an unknown mediator.

The levels of Stat3 and Fer dropped significantly in C2C12 cells after 72 hr of serum starvation (FIG. 5B and FIG. 6A lanes 1-4). This downregulation was abolished in cells treated with the proteasome inhibitor GM132 (FIG. 5B and FIG. 6A lanes 5-8s), suggesting that Fer and Stat3 are prone to proteasomal degradation. Proteasomal downregulation of an inactive Fer enzyme (Craig, A. W., Zimgibl, R., Williams, K., Cole, L. A. & Greer, P. A. (2001) *Mol. Cell Biol.* 21, 603-613) and of Stat3 (Daino, H., Matsumura, I., Takada, K., Odajima, J., Tanaka, H., Ueda, S., Shibayama, H., Ikeda, H; Hibi, M., Machii, T et al. (2000) *Blood* 95, 2577-2585), has been suggested before. Interestingly, both Fer and Stat3 were dephosphorylated on tyrosine and were both inactive, when they formed a complex with TMF/ARA160.

The association of TMF/ARA160 with Fer and Stat3 was most prominent after 24 and 48 hr of serum starvation and increased significantly in cells treated With GM132. This profile preceded but also overlapped the downregulation of Fer and Stat3, which was most apparent after 48 and 72 hr of serum starvation. Thus, association with TMF/ARA160 could serve as an intermediate and preceding step in the degradation of Stat3 and Fer, under serum starvation. This notion is supported by the fact that the TMF/ARA160 complex contained ubiquitinated proteins after 24 hr of serum starvation (FIG. 7 lane 2). Another piece of supporting evidence stems from the fact that serum starvation did not lead to the degradation of Stat3, in cells that did not release of TMF/ARA160 from the Golgi. TMF/ARA160 may be a part of a complex, analogous to the ubiquitination complex SCF (DeSalle, L. M. & Pagano, M. (2001) *FEBS Left* 490, 179-189), that ubiquitinates and recruits a defined set of cellular proteins, to the proteasome degradation machinery. Sequence analysis did not reveal F-box or E3-ligase motifs in TMF/ARA160. However, TMF/ARA160 could serve as a scaffold protein in the assembly of specific ubiquitin-ligase. A similar role was attributed to Elongin B C (Conaway, J. W., Kamura, T. & Conawvay, R. C. (1998) *Biochim. Biophys. Acta* 1377, M49-M54) and to Muf1 that like TMF/ARA160 contains leucine rich stretches (Garcia, J. A., On, S. H., Wu, F., Lusis, A. J., Sparkes, R. S. & Gaynor, R. B. (1992) *Proc. Natl. Acad Sci. USA* 89, 9372-9376) which are essential for its scaffolding activity (Kamura, T., Burian, D., Yan, Q., Schmidt, S. L, Lane, W. S., Querido, E, Branton, P. E., Shilatifard, A, Conaway, R. C. & Conaway, J. W. (2001) *J. Biol. Chem*). Interestingly, TMF/ARA160 itself contains two potential cyclin degradation boxes that could direct it, to a ubiquitin-mediated proteasomal degradation (Garcia, J. A., Ou, S. H., Wu, F., Lusis, A, J., Sparkes, R. S. & Gaynor, R. B. (1992) *Proc. Nail. Acad. Sci. USA* 89, 9372-9376). Hence, the levels of TMF/ARA160 itself could be regulated by proteasomal degradation As mentioned above, cyclin D1 is also a component of the cytoplasmic TMF/ARA160 complexes, in C2C12 cells. However the decline in the cyclin D1 levels in serum-starved C2C12 cells, was-relatively moderate. Therefore one can not exclude the possibility that the decrease in the cyclin D1 levels result from the degradation of Stat3 which serves as an positive activator of the cyclin D1 gene (Bromberg, J. F., Wrzeszcznska, M. H., Devgan, G., Zhao, Y., Pestell, R. G., Albanese, C. & Darnell. J. E., Jr. (1999) *Cell* 98, 295-303). The association of TMF/ARA160 with defined cytoplasmic proteins is specific since TMF/ARA160 did not associate with Stat1 which is linked to the arrest of cell-growth arrest (Zhou, Y., Wang, S., Gobl, A. & Oberg, K. (2001) *Oncology* 60, 330-338). Thus TMF/ARA160 associates specifically with proliferation promoting factors in serum-starved C2C12 cells, and may be involved in their downregulation.

C2C12 myoblasts undergo growth arrest and myogenic differentiation upon serum starvation (Craig, A. W., Zimgibl, R., Williams, K., Cole, L A. & Greer, P. A. (2001) *Mol. Cell Biol.* 21, 603-613) However, the release of TMF/ARA160 from the Golgi and the down regulation of Fer and Stat3, does not seem to be necessarily linked to the myogenic differentiation process, since other inducers of myogenic differentiation (Salzberg, S., Vilchik, S., Cohen, S., Heller, A. & Kronfeld-Kinar, Y. (2000) *Exp. Cell Res.* 254, 45-54; Cohen, R., Valverde, A. M., Benito, M. & Lorenzo, M. (2001) *J. Cell Physiol* 186, 82-94), did not lead to the time dependent degradation of these proteins.

It should also be stressed that an efficient release of TMF/ARA160 from the Golgi, in all mammalian cell-lines that were grown under low serum conditions was not seen.

TMF/ARA160 seems therefore to be involved in downregulation of key, proliferation promoting factors like Stat3, under defined cellular conditions. One of these could be deprivation of growth factors, that like in C2C12 cells, leads to irreversible growth arrest. This may imply a novel role for the Golgi apparatus in the modulation of cell-growth. The Golgi, like the mitochondria (Scheffler, I. E. (2001) *Adv. Drug Deliv. Rev.* 49, 3-26), seems to harbor cellular downregulator(s) that are released and activated at defined cellular conditions. Interestingly, disintegration of the Golgi by BFA in cancer cells, led to the degradation of key cell-cycle regulators and consequent cell death (Chapman, J. R., Tazaki. H., Mallouh, C. & Konno, S. (1999) *Mol. Urol.* 3, 11-16).

Example Two

Levels of TMF/ARA160 in Normal, Benign and in Malignant Human Tissues

After confirming the quality and reliability of the αTMF/ARA160 antibodies, we turned to assess the relative levels of TMF/ARA160 in normal, benign and in malignant human tissues. Whole cell protein extracts were prepared from normal human tissues, from benign tumors and from various human tumors using a Nonidet P-40 (NP40) lysis buffer (1% NP40, 0.5% Sodium deoxycholate, 20 mM Tris.HCl pH 7.5, 150 mM NaCl, 1 mM EDTA and 2 mM Na2VO4), as was described before (Priel-Halachmi, S. et al. (2000) J. Biol. Chem. 275: 28902-28910.) The relative levels of TMF/ARA160 were then analyzed in benign and in solid malignant human tumors. Protein samples (30 µg) from each preparation were resolved in a 7% SDS poly acrylamide gel (SDS-PAGE), blotted onto a nitrocellulose membrane and were then reacted with the affinity purified αTMF/ARA160 antibodies.

Figure 8:
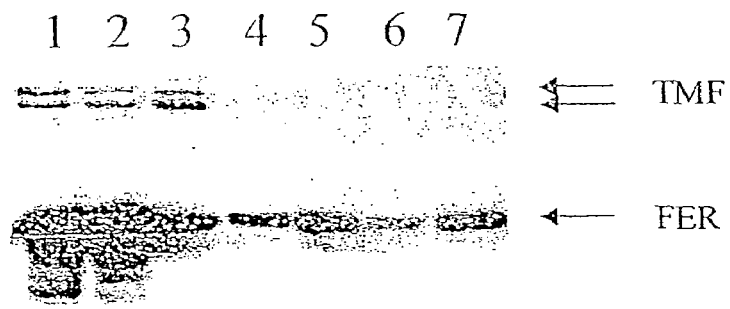
FIG. 8 is an immunoblot, using the methods and compositions of the present invention, illustrating TMF/ARA160 levels in benign and in malignant human menigiomas.

FIG. 8 is an immunoblot illustrating TMF/ARA160 levels in benign and in malignant human menigiomas. 30 mg protein from: benign (lanes 1-3) and from malignant menigiomas (lanes 4-7), were resolved by 7% SDS-PAGE and reacted with αTMF/ARA160 (upper panel) or with αFER(p94fer) (lower panel), antibodies. Two forms of TMF/ARA160 could be seen in the analyzed samples (indicated by two arrows on the right side of the upper panel).

While three benign human menigiomas accumulated relatively high levels of TMF/ARA160 (FIG. 8 upper panel lanes 1-3), the levels of the protein were significantly lower in 5 malignant menigiomas analyzed (FIG. 8 upper panel, lanes 4-7). Similarly, very low levels of TMF/ARA160 were seen also in two malignant human glioblastomas that were analyzed Interestingly the levels of the tyrosine kinase p94fer which was found to be essential for the proliferation of cancer cells (Allard, P. et al. (2000) Mol. Cell. Endocrinol. 159:63-77; Orlovsky, K. et al. (2000) Biochemistry 39:11084-11091), were similar in both benign and in malignant tumors (FIG. 8 lower panel).

Figure 9:
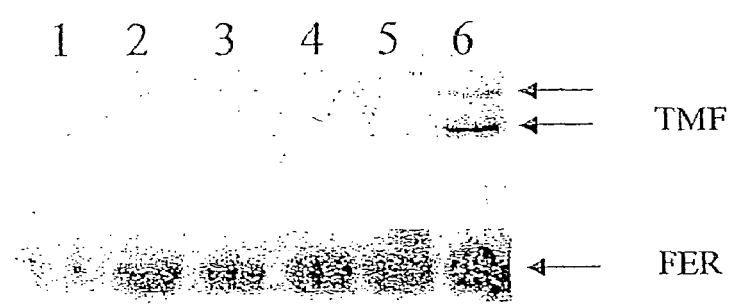
FIG. 9 is an immunoblot, using the methods and compositions of the present invention, showing that TMF/ARA160 is not detected human malignant prostate xenografts.

To further extend our analysis, the levels of TMF/ARA160 were determined in four human xenografts which were derived from four independent prostate tumors. FIG. 9 shows that TMF/ARA160 is not detected human malignant prostate xenografts. Proteins from five independent prostate cancer xenografts (lanes 1-5) and from the myogenic cell line C2C12 (lane 6), were resolved in SDS-PAGE and were then reacted with αTMF/ARA160 (upper panel) or with a αFER antibodies (lower panel). While the tyrosine kinase p94fer was clearly detected in all the xenografts (FIG. 9 lower panel), no TMF/ARA160 could be found in the analyzed preparations (FIG. 9 lanes 1-5, upper panel). To compare the levels of TMF/ARA160 in malignant prostate cells to its level in transformed but non-malignant prostate cells, whole cell protein extracts were prepared from four different prostate cell lines. These were the benign prostate hyperplasia cell line-BPH1, the androgen sensitive and PSA producing prostate cancer cell line LNCAP which was derived from a metastasis of a prostate carcinoma to the lymph-node, the DU-145 cell-line which was derived from metastasis of prostate carcinoma to the vertebra and the PC-3 cell line which was derived from a prostate cancer metastasis to the brain. Protein samples from the four prostate cell-lines were resolved by 7% SDS-PAGE mid were reacted with the affinity purified αTMF/ARA160 antibodies, in a Western-blot analysis.

Figure 10:
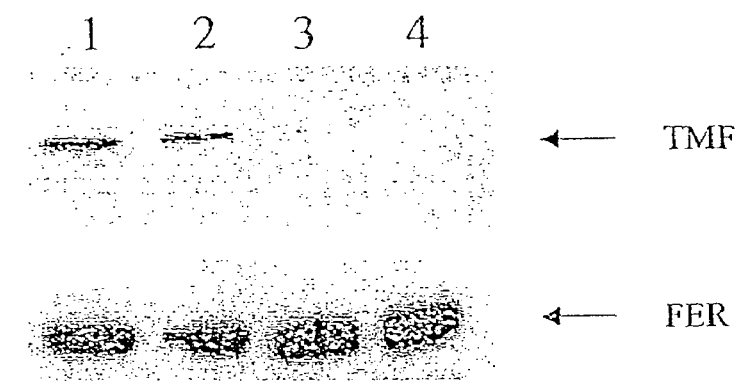
FIG. 10 is an immunoblot, using the methods and compositions of the present invention, showing the accumulation of TMF/ARA160 in human prostate cell-lines.

FIG. 10 illustrates the accumulation of TMF/ARA160 in human prostate cell-lines Proteins from: BPH1 (benign cell-line, lane 1); LNCAP (androgen sensitive, prostate cancer cell-line, lane 2)); DU-145 (androgen insensitive, prostate cancer cell-line, lane 3) and from PC-3 (androgen insensitive, prostate cancer cell-line, lane 4) cells are shown.

TMF/ARA160 was prominently detected in the benign cell line BPH1 and in the androgen sensitive cell line LNCAP (FIG. 10 lanes 1 and 2). However, TMF/ARA160 was barely detected in the DU-145 and PC-3 cell lines (FIG. 10 lanes 3 and 4) which do not respond to androgens and are therefore considered as a relatively early stage of the a prostate carcinoma.

Figure 11:
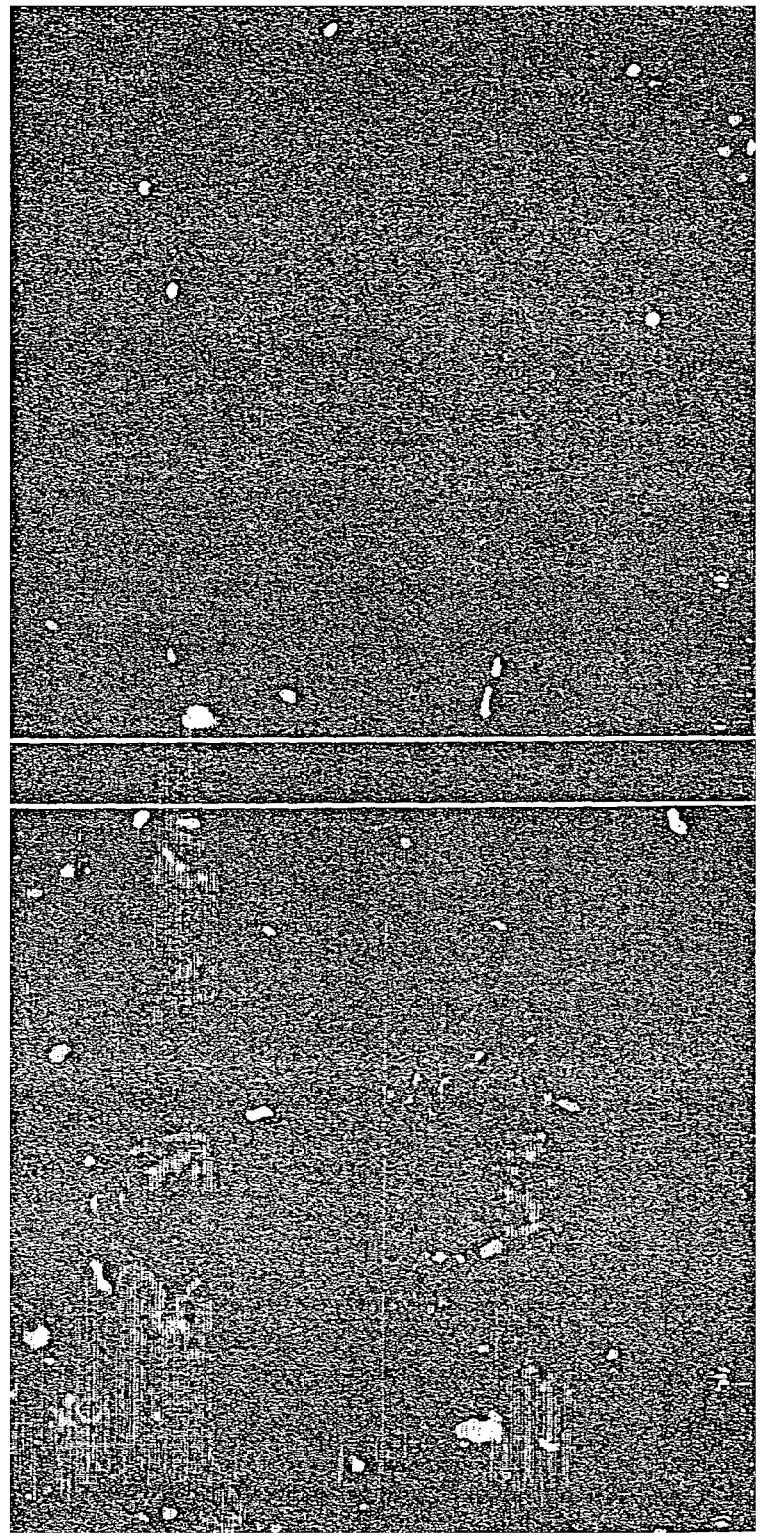
FIG. 11 is an immunocytochemical analysis, using the methods and compositions of the present invention, of prostate sections.

FIG. 11 shows comparative immunohistochemistry of prostate sections: normal prostate tubules (left) and malignant tubules (right). Staining of the internal epithelial cells is clearly evident and seen in the normal sample (left panel), and staining is absent in the malignant tissue tubules (right panel).

Example Three

Downregulation of the Cellular Level of Fer Protein, Growth Arrest and Death of Prostate Cancer Cells in Culture by siRNA Transfection In Vitro siRNA Sequences:

The target sequences in the fer mRNA were selected and siRNA duplexes designed according to the guidelines described hereinabove. Two separate siRNA duplexes were used and were obtained from commercial sources (Dharmacon, Lafayette, Colo.). The first target sequence (SEQ ID NO: 1) was (5'-) AAAGAAAUUUAUGGCCCUGAG (-3') and begins 84 nucleotides from the start codon. The siRNA duplex used for this sequence is referred to as the 5' siRNA. The sense siRNA oligonucleotide (SEQ ID NO:2) has the sequence (5'-) AGAAAUUUAUGGCCCUGAGdTdT (-3') and the antisense oligonucleotide (SEQ ID NO:3) has the sequence (5'-) CUCAGGGCCAUAAAUUUCUdTdT (-3').

The duplex formed is shown below:

```
                        5' siRNA siRNA Duplex

A.G.A . A.A.U . U.U.A . U.G.G . C.C.C . U.G.A . G.dT.dT dT.dT . U.C.U . U.U.A . A.A.U . A.C.C . G.G.G . A.C.U . C
```

The second target sequence (SEQ ID NO:4) was (5'-) AAUCGCCCUAAGUUCAGUGAA (-3') and begins 2407 nucleotides from the start codon. The siRNA duplex used for this sequence is referred to as the 3' siRNA. The sense siRNA oligonucleotide (SEQ ID NO:5) has the sequence (5'-) UCGCCCUAAGUUCAGUGAAdTdT (-3') and the antisense oligonucleotide (SEQ ID NO:6) has the sequence (5'-) UUCACUGAACUUAGGGCGAdTdT (-3'). The duplex formed is shown below:

```
                        3' sIRNA sIRNA Duplex

U.C.G . C.C.C . U.A.A . G.U.U . C.A.G . U.G.A . A.dT.dT dT.dT . A.G.C . A.G.C . G.G.G . A.U.U . C.A.A . G.U.C . A.C.U . U
```

Protocol for Cell Line Transfection

PC3 cells (a cell line derived from a prostate cancer metastasis to the brain) were counted and seeded on Petri dishes (diameter–6 cm) and were grown in RPMI+10% FCA medium in 37° C. $CO_2$ 5% for 20-24 hours. 30 µl siRNA (see above) from 20 µM stock solution was mixed with 300 µl OptiMEM (Gibco-Invitrogen) medium and incubated in room temperature for 5 minutes. In a separate tube, 20 µl Metafectene (Biontex) was mixed with 160 µl OptiMEM and also incubated in room temperature for 5 min. Then the contents of the 2 tubes were mixed (510 µl) and incubated for 15-20 min in room temperature for production of lipid-siRNA complexes. The medium from the cells was removed and the cells covered with 129 µl OptiMEM, FCS 200 µl and 510 µl lipids—siRNA complexes. Final concentration of siRNA in the Petri dish is 300 nM 8 hours later 1800 µl Optimem and 200 µl FCS were added to the cells. After 72 hours the cells were scraped and proteins extracted.

Results

Figure 12:
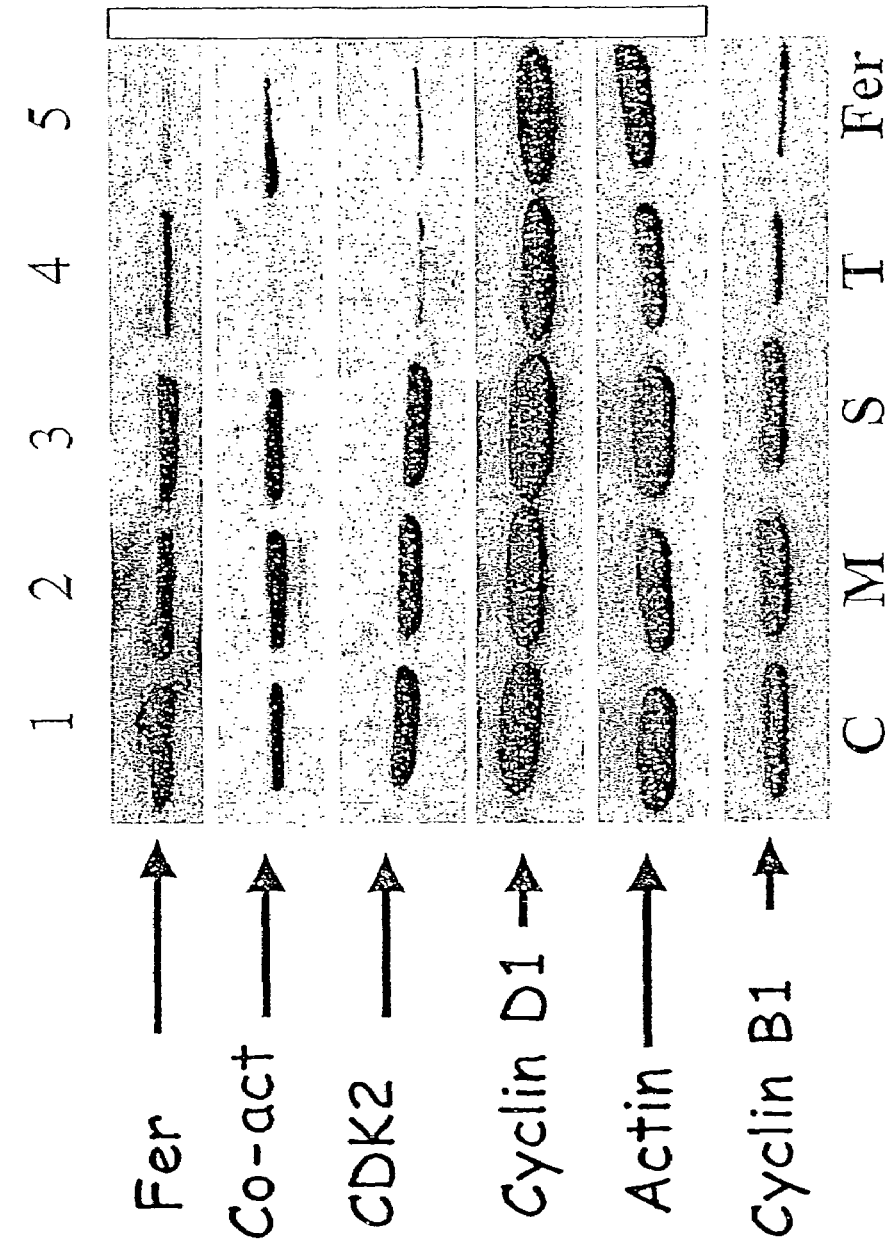
FIG. 12 illustrates protein levels of various proteins in PC3 cells in culture after siRNA treatment according to the present invention.

FIG. 12 illustrates protein expression of various proteins (fer, TMF/ARA160 [labeled as co-act], CDK2, cyclin D1, actin, and cyclin B1 respectively) in PC3 cells in culture after treatment with 5' siRNA. Lane 1 (C) is the control lane—protein expression in untreated PC3 cells, lane 2 (M)-cells treated with the transfection reagent alone without any siRNA, lane 3 (S)-cells treated with an siRNA duplex for an unrelated gene, lane 4 (T)-cells treated with siRNA directed to the TMF/ARA160 mRNA, and lane 5 (Fer)-cells treated with the 5' siRNA duplexe against fer as above. Following treatment with the 5' siRNA duplexes directed against fer mRNA, as can be seen in lane 5, there is a marked diminution in the protein levels of fer. Furthermore there is also noted a decrease in levels of other growls promoting factors, cell cycle control proteins CDK2 and cyclin B1. Such decreases in growth promoting factors are expected to result in the decrease in tumor cell proliferation.

Figure 13:
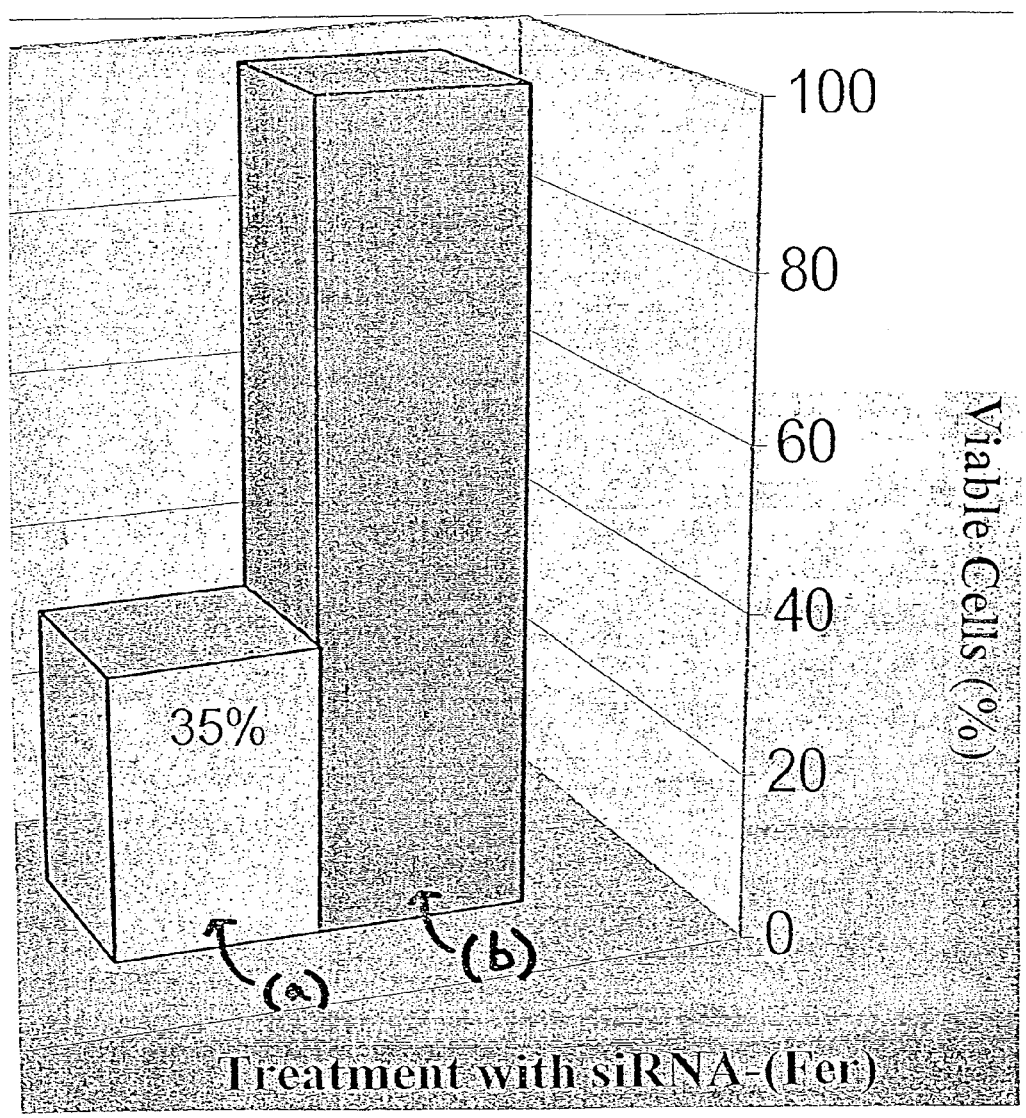
FIG. 13 is a graph illustrating the percentage of viable PC3 cells in culture after siRNA treatment according to the present invention.

FIG. 13 is a graph illustrating the percentage of viable PC3 cells in culture after 5' siRNA treatment. Me bar on the left (a) illustrates the percentage of viable cells in culture after treatment with 5' siRNA directed against fer mRNA compared to cells treated with the transfection reagent alone (bar b on the right). As can be seen, after treatment with 5' siRNA directed against fer mRNA, there was a marked decrease in cell viability and only 35% of the cells in culture were viable.

Figure 14A:
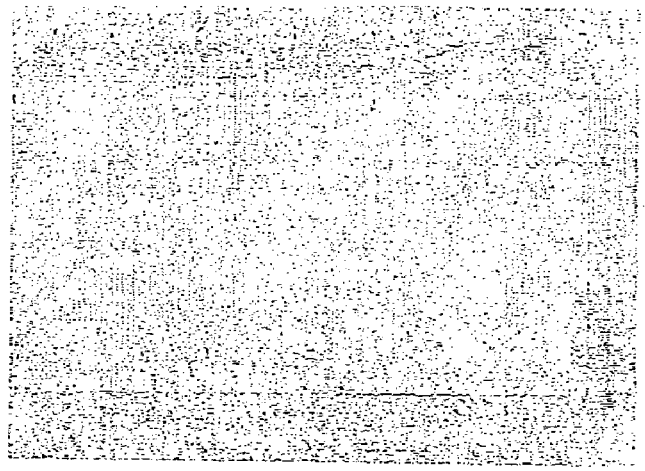
FIG. 14 is a series of photomicrographs of PC3 cells in culture after siRNA treatment according to the present invention (a) compared to control cultures (b and c); and, FIG. 15 is a graph illustrating tumor growth in a mouse following siRNA treatment according to the present invention (b) compared to that in a control mouse not treated (a).
Figure 14B:
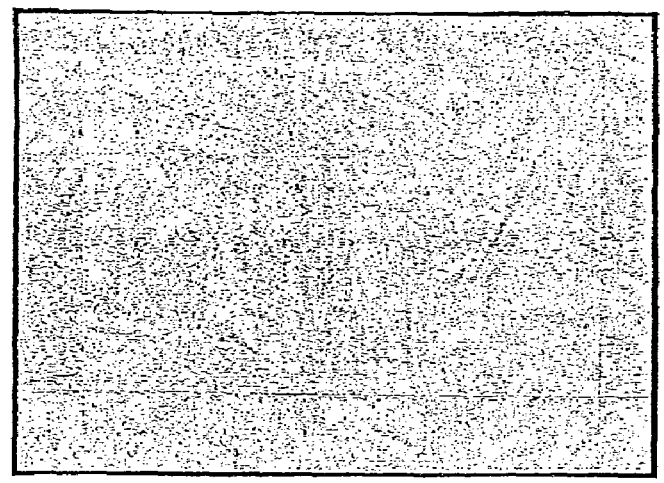
Figure 14C:

The growth arrest and cell death can also be seen directly in FIG. 14, which is a series of photomicrographs of PC3 cells in culture; The photomicrograph in panel a is of cells after 5' siRNA treatment resulting in downregulation of fer, and is compared to those of control cultures (b and c) not treated With siRNA directed against fer mRNA.

Thus, it can be seen that short interfering RNAs (siRNA) directed toward the Fer mRNA degraded fer mRNA and consequently downregulated the cellular level of the Fer protein. This led to the growth arrest of the prostate cancer cells and to their subsequent death.

Example Four

In Vivo Transfection of siRNA to Fer Leads to Diminished Tumor Growth Tumor Induction in Mice Approximately $3*10^6$ PC3 cells in 100 µl Hank's Balanced Salt Solution (Sigma) are mixed with 100 µl Matrigel (BD Bioscience) just prior to injection. The mixture is injected subcutaneously in CD1-nude mice for tumor induction. After 3-5 days, a pea size tumor has developed.

Preparation of siRNA for Injection:

Two different protocols for preparation of siRNA complexes for direct injection in vivo were employed with similar efficacy. The siRNA duplexes used were those described above in example three.

A. 0.5 µl TransIT-TKO transfection reagent (Mirus, Madison, Wis.) is added to 13.33 µl OptiMEM and incubated in room temperature for 5 min. Then 0.5 µl siRNA is added to the solution for further incubation at room temperature following addition of 35.5 µl OptiMEM to a final volume of 50 µl.

B. 0.5 µl Mirus TransIT In Vivo is added to 0.5 µl siRNA and 49 µl of Water for Embryo Transfer (Sigma) to a final volume of 50 µl.

Injection of siRNA into Mice

The tumor was then injected locally in 2-3 spots, with 50 µl 5' siRNA in either the siRNA carrier TransIT-TKO or Mirus TransIT In Vivo (Mirus) as above. Injection was made on day 3 and the surface area of the tumor measured daily.

Results

Figure 15:
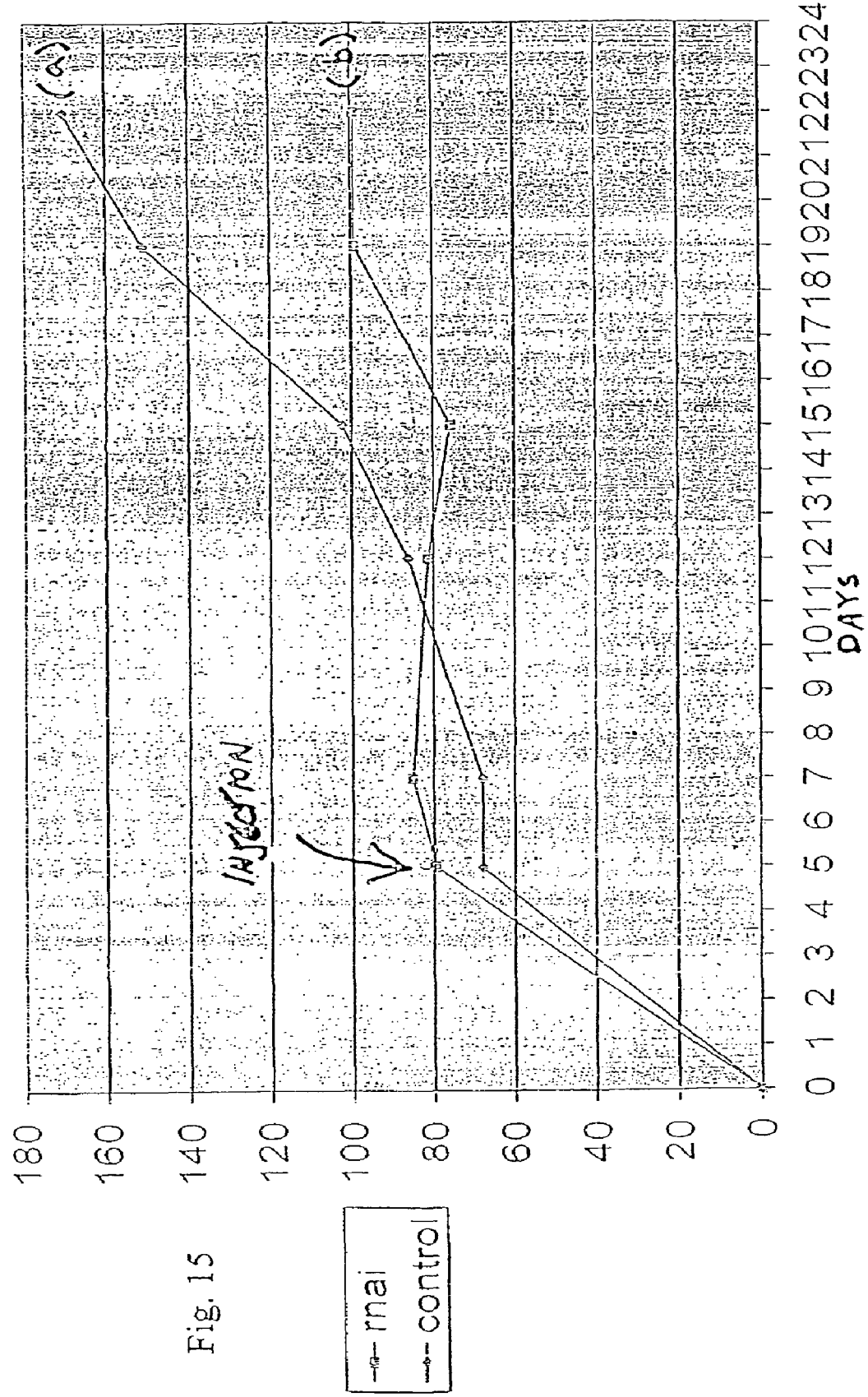

FIG. 15 is a graph illustrating tumor growth (surface area) in a mouse following 5' siRNA treatment according to the present invention (b) compared to that in a control mouse not treated (a). As can be seen, the treated tumor demonstrated diminished growth and its size was over 40% smaller than the control tumor after 3 weeks. Thus in vivo administration of siRNA directed against fer mRNA resulted in an effective treatment of the cancer explant with demonstrated decrease in tumor size and growth.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification, or referenced in those mentioned, are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A compound 21 nucleobases in length comprising SEQ ID NO:2.

2. A compound 21 nucleobases in length comprising SEQ ID NO:3.

3. A short interfering ribonucleic acid molecule comprising a duplex molecule of two compounds, wherein the first compound is a compound 21 nucleobases in length comprising SEQ ID NO:2, and the second compound is compound 21 nucleobases in length comprising SEQ ID NO:3.

4. A compound 21 nucleobases in length comprising SEQ ID NO:5.

5. A compound 21 nucleobases in length comprising SEQ ID NO:6.

6. A short interfering ribonucleic acid molecule comprising a duplex molecule of two compounds, wherein the first compound is a compound 21 nucleobases in length comprising SEQ ID NO:5, and the second compound is compound 21 nucleobases in length comprising SEQ ID NO:6.

* * * * *

```
                        SEQUENCE LISTING

<160> NUMBER OF SEQ ID NOS: 6

<210> SEQ ID NO 1
<211> LENGTH: 21
<212> TYPE: RNA
<213> ORGANISM: Homo sapiens

<400> SEQUENCE: 1
aaagaaauuu auggcccuga g                                              21

<210> SEQ ID NO 2
<211> LENGTH: 21
<212> TYPE: RNA
<213> ORGANISM: Artificial
<220> FEATURE:
<223> OTHER INFORMATION: Synthetic oligonucleotide

<400> SEQUENCE: 2
agaaauuuau ggcccugagu u                                              21

<210> SEQ ID NO 3
<211> LENGTH: 21
<212> TYPE: RNA
<213> ORGANISM: Artificial
<220> FEATURE:
<223> OTHER INFORMATION: Synthetic oligonucleotide

<400> SEQUENCE: 3
uuucuuuaaa uaccgggacu c                                              21

<210> SEQ ID NO 4
<211> LENGTH: 21
<212> TYPE: RNA
<213> ORGANISM: Homo sapiens

<400> SEQUENCE: 4
aaucgcccua aguucaguga a                                              21

<210> SEQ ID NO 5
<211> LENGTH: 21
<212> TYPE: RNA
<213> ORGANISM: Artificial
<220> FEATURE:
<223> OTHER INFORMATION: Synthetic oligonucleotide

<400> SEQUENCE: 5
ucgcccuaag uucagugaau u                                              21
```

```
<210> SEQ ID NO 6
<211> LENGTH: 21
<212> TYPE: RNA
<213> ORGANISM: Artificial
<220> FEATURE:
<223> OTHER INFORMATION: Synthetic oligonucleotide

<400> SEQUENCE: 6
uuagcgggau ucaagucacu u                                              21
```